United States Patent
Xuan et al.

(10) Patent No.: US 9,939,359 B2
(45) Date of Patent: Apr. 10, 2018

(54) METHOD OF MEASUREMENT AND DETERMINATION ON FRACTURE TOUGHNESS OF STRUCTURAL MATERIALS AT HIGH TEMPERATURE

(71) Applicants: EAST CHINA UNIVERSITY OF SCIENCE AND TECHNOLOGY, Shanghai (CN); SHANGHAI ELECTRIC POWER EQUIPMENT CO., LTD. SHANGHAI STEAM TURBINE FACTORY, Shanghai (CN)

(72) Inventors: Fuzhen Xuan, Shanghai (CN); Haitao Wang, Shanghai (CN); Qiongqi Wang, Shanghai (CN); Linbo Mei, Shanghai (CN); Xia Liu, Shanghai (CN); Yuhui Huang, Shanghai (CN)

(73) Assignees: EAST CHINA UNIVERSITY OF SCIENCE AND TECHNOLOGY, Shanghai (CN); SHANGHAI ELECTRIC POWER EQUIPMENT CO., LTD. SHANGHAI STEAM TURBINE FACTORY, Shanghai (CN)

( * ) Notice: Subject to any disclaimer, the term of this patent is extended or adjusted under 35 U.S.C. 154(b) by 99 days.

(21) Appl. No.: 14/915,659

(22) PCT Filed: Sep. 25, 2014

(86) PCT No.: PCT/CN2014/087373
§ 371 (c)(1),
(2) Date: Mar. 1, 2016

(87) PCT Pub. No.: WO2016/045024
PCT Pub. Date: Mar. 31, 2016

(65) Prior Publication Data
US 2016/0299046 A1 Oct. 13, 2016

(51) Int. Cl.
*G01N 3/08* (2006.01)
*G01N 3/42* (2006.01)
(Continued)

(52) U.S. Cl.
CPC .............. *G01N 3/18* (2013.01); *G01N 3/00* (2013.01); *G01N 3/08* (2013.01); *G01N 3/28* (2013.01);
(Continued)

(58) Field of Classification Search
CPC .. G01N 3/18; G01N 3/28; G01N 3/08; G01N 2203/0017; G01N 2203/0069; G01N 3/00;
(Continued)

(56) References Cited

U.S. PATENT DOCUMENTS 5,602,329 A * 2/1997 Haubensak .............. G01N 3/08
73/105
7,487,051 B2 * 2/2009 Kim ......................... G01N 3/42
702/33
(Continued)

FOREIGN PATENT DOCUMENTS

CN 101975695 A 2/2011
CN 102435513 A 5/2012
(Continued)

OTHER PUBLICATIONS

International Search Report from PCT/CN2014/087373 dated Jun. 12, 2015.
(Continued)

*Primary Examiner* — Harshad R Patel
*Assistant Examiner* — Brandi Hopkins
(74) *Attorney, Agent, or Firm* — Millen White Zelano and Branigan, PC; John Sopp

(57) ABSTRACT

Disclosed is a method of measurement and determination on fracture toughness of structural materials at high tempera-
(Continued)

ture, comprising: preliminary assessing the ductility of a material based on a high-temperature uniaxial tensile test and the fracture characteristic; designing and manufacturing a CT specimen; conducting a monotonic loading fracture test on the CT specimen at high temperature; modifying a load-displacement curve output by a testing machine; determining a passivation coefficient M for the crack of the structural material; reversely recursing instant load-displacement data pairs corresponding to the instant crack length; calculating a J_R crack extension resistance curve of the tensile test; examining the validity of the J_R crack extension resistance curve and the fracture toughness $J_{IC}$; calculating the fracture toughness per equivalent of the structural material $K_{IC}$. The present invention overcomes the difficulty of placing an extensometer inside a high-temperature furnace.

4 Claims, 12 Drawing Sheets

(51) Int. Cl.
    *G01N 3/00*         (2006.01)
    *G01N 3/18*         (2006.01)
    *G01N 3/28*         (2006.01)

(52) U.S. Cl.
    CPC ............... *G01N 2203/006* (2013.01); *G01N 2203/0017* (2013.01); *G01N 2203/0069* (2013.01)

(58) Field of Classification Search
    CPC ............... G01N 2203/006; G01N 3/38; G01N 2203/0051; G01N 2203/0073; G01N 3/36; G01N 2203/0062; G01B 21/02
    See application file for complete search history.

(56) References Cited

U.S. PATENT DOCUMENTS

| | | | |
|---|---|---|---|
| 8,606,532 B2* | 12/2013 | Hiwatashi | G01M 5/0033 702/42 |
| 8,990,028 B2* | 3/2015 | Yonemura | G01N 3/00 702/35 |
| 9,305,121 B2* | 4/2016 | Yao | E21B 43/26 |
| 2008/0078479 A1* | 4/2008 | Xue | C21D 6/02 148/508 |

FOREIGN PATENT DOCUMENTS

| | | |
|---|---|---|
| CN | 102494959 A | 6/2012 |
| CN | 103604694 A | 2/2014 |
| JP | 2003106964 A | 4/2003 |

OTHER PUBLICATIONS

English Version of Written Opinion Report from PCT/CN2014/087373 dated Jun. 9, 2015.
Written Opinion Report from PCT/CN2014/087373 dated Jun. 9, 2015.

* cited by examiner

METHOD OF MEASUREMENT AND DETERMINATION ON FRACTURE TOUGHNESS OF STRUCTURAL MATERIALS AT HIGH TEMPERATURE

FIELD OF INVENTION

The present invention relates to a testing technique of mechanical properties of materials, especially relates to a method of measurement and determination on fracture toughness of structural materials at high temperature.

PRIOR ARTS

There is a variety of special mechanical equipment such as distillation columns, refining furnaces, reactor pressure vessels, boilers, turbines, engines, etc. in chemical engineering, metallurgy, energy, transportation and other industrial fields. Generally, this kind of mechanical equipment has a complex structure, bears a variety of loading, and often runs under a harsh environment of high temperature, high pressure, corrosive medium or the like. Forced by the complex stress and harsh service environment, this kind of mechanical equipment is prone to produce defects, become damaged and fail. Some of the damages and failure may cause the equipment to stop running, while some may lead to tremendous economic losses and casualties. Based on this, it is of great significance to ensure a safety service of the mechanical equipment during its designed life cycle for industrial operation, cost saving and personnel safety in extreme environment.

The mechanical equipment serviced under harsh environment of high temperature is generally made from materials with high ductility. To ensure the safety use of the mechanical equipment, it needs to obtain the fracture toughness (crack resistance curve, plane strain fracture toughness and fracture toughness per equivalent) of structural materials in high-temperature service environment so as to achieve damage tolerance of a structure, proceed integrity analysis and evaluation of the structure having defects, as well as make residual strength analysis of the structure and so on. The fracture toughness is characterized by the crack resistance and expansion ability of structural materials in given environment, which is determined by a fracture test. Traditional fracture toughness test generally includes a multiple-specimen method and a single-specimen method, wherein the multiple-specimen method is conducted by measuring multiple specimens (generally more than six) with same size. This method requires more manual power and material resources which results in high testing cost, and obtained data points usually exhibit a certain dispersion. As for materials with high ductility, there may occur a wide extent of passivation and deformation on the crack tip in the loading process. On this case, it is difficult to obtain the test points in critical areas through the multiple-specimen method. The single-specimen method is conducted by measuring one or two specimens to obtain crack extension resistance curve and the fracture toughness. Typical single-specimen method includes an elastic unloading compliance method and a potential method. It is confirmed by the experiments that the elastic unloading compliance method and the potential method put forward higher requirements on skills, and the reliability of the results obtained by this two methods depends on the accuracy of the testing instrument and the performance characteristics of the tested material in a large extent. Materials with high ductility tend to produce serious passivation and crack closure on the crack tip of the specimen, which limits the judgment and the application of the elastic unloading compliance method and the potential method.

At high temperature, the size of a furnace, the accuracy of a high-temperature extensometer and a sensing device, the geometric characteristics of a specimen loaded, the employment of passivation parameters for materials, etc. bring out difficulties for testing high-temperature fracture toughness. Moreover, the ductile structural materials will produce more severe crack closure and stress relaxation on the crack tip when exposed to high temperature. In this case, it is difficult or even impossible to obtain the fracture toughness at high temperature by both the multiple-specimen method and the single-specimen method. Currently, in order to meet the safety requirements of industrial operation, it's highly desirable to develop a new method which is reliable and suitable for the measurement and determination on the fracture toughness of structural materials at high temperature.

CONTENT OF THE PRESENT INVENTION

The present invention provides a method of measurement and determination on fracture toughness of structural materials at high temperature to overcome the defects in the prior art.

The present invention solves the above technical problem by the following technical solution: a method of measurement and determination on fracture toughness of structural materials at high temperature, wherein the method comprises:

Step 1. conducting a high-temperature tensile test on a standard tensile specimen of a structural material to obtain high-temperature tensile mechanical properties of the material, and determining that the material exhibits a ductile fracture behavior;

Step 2. preliminarily estimating the fracture toughness $K_{IC}$ of the structural material at high temperature to obtain the width (W) and thickness (B) of the compact tension (CT) specimen, wherein, $$J_{IC} = \frac{K_{IC}^2(1-v^2)}{E},$$
$$W = a_0 + b_0 \geq 2 \times 10 J_{IC}/\sigma_Y,$$
$$\sigma_Y = \frac{(\sigma_{ys} + \sigma_{uts})}{2},$$
$$2 \leq W/B \leq 4$$

E, $v$ stand for elastic modulus and Poisson ratio of the material respectively, the unit of E is $MP$, $a_0$, $b_0$ stand for initial crack length and initial ligament size of the CT specimen respectively, the unit for $a_0$ and $b_0$ is mm, $\sigma_{ys}$, $\sigma_{uts}$ stand for yield strength and tensile strength of the structural material respectively, the unit for $\sigma_{ys}$ and $\sigma_{uts}$ is MPa;

Step 3. inducing a fatigue crack on the CT specimen through a high frequency fatigue testing machine, then grooving a side slot with a depth of 10% B at both sides of the specimen with a crack surface along the thickness direction;

Step 4. measuring the thickness (B) and width (W) of the CT specimen, and placing the specimen into a heating equipment with a furnace, and heating;

Step 5. turning on an INSTRON or MTS testing machine, monotonic loading the specimen, and obtaining a load-displacement curve of the specimen by a load displacement transmission device on the testing machine:

Step 6. cooling the CT specimen to room temperature, opening furnace's cavity, tensing the specimen till fracture through a testing machine, then measuring an initial crack length $a_0^i$ and a final crack length $a_f^i$ at nine spots on the crack surface by an optical microscopy or a camera to obtain an initial average crack length $a_0$ and a final crack length $a_f$ of the crack, wherein, $$a_0 = \frac{1}{8}\left[\frac{1}{2}(a_0^1 + a_0^9) + \sum_{i=2}^{8} a_0^i\right],$$

$$a_f = \frac{1}{8}\left[\frac{1}{2}(a_f^1 + a_f^9) + \sum_{i=2}^{8} a_f^i\right];$$

Step 7. obtaining an initial elastic compliance $C_{LL(a_0)}$ of the specimen based on the sizes of the specimen and the crack and the elasticity modulus E of the structural material at high temperature, wherein, $$C_{LL(a_0)} = \frac{1}{EB_e}\left(\frac{W+a_0}{W-a_0}\right)^2\left[2.1630 + 12.219\left(\frac{a_0}{W}\right) - 20.065\left(\frac{a_0}{W}\right)^2 - 0.9925\left(\frac{a_0}{W}\right)^3 + 20.609\left(\frac{a_0}{W}\right)^4 - 9.9314\left(\frac{a_0}{W}\right)^5\right],$$

$B_e$ stands for an effective thickness of the CT specimen, the unit for which is mm;

Step 8. modifying the testing errors caused by load contacts, local indentation, piston rigidity of the testing machine, rigidity of the fixture, etc., on the load-displacement curve to obtain a modified load-displacement curve;

Step 9. calculating a passivation coefficient M of the material according to the mechanical properties of the material;

Step 10. calculating a modified crack length $a_{b(i)}$ corresponding to each load spot based on the modified load-displacement curve, the initial average crack length $a_0$ and the passivation coefficient M of the material, wherein, $$f\left(\frac{a_0}{W}\right) = \frac{\left[\left(2 + \frac{a_0}{W}\right)\left(0.886 + 4.64\left(\frac{a_0}{W}\right) - 13.32\left(\frac{a_0}{W}\right)^2 + 14.72\left(\frac{a_0}{W}\right)^3 - 5.6\left(\frac{a_0}{W}\right)^4\right)\right]}{\left(1 - \frac{a_0}{W}\right)^{1.5}},$$

$$K_{(i)} = \frac{P_i}{(BB_N W)^{0.5}} f\left(\frac{a_0}{W}\right),$$

$$J_{el(i)} = \frac{K_{(i)}^2 (1-\nu^2)}{E},$$

$$A_{pl(i)} = A_i - A_{el(i)} = A_i - \frac{P_i^2}{2k},$$

$$\eta_{pl} = 2 + 0.522 b_0/W = 2 + 0.522(W - a_0)/W,$$

$$J_{pl(i)} = \frac{\eta_{pl} A_{pl(i)}}{B_N b_0},$$

$$J_i = J_{el(i)} + J_{pl(i)},$$

$$a_{b(i)} = a_0 + \frac{J_i}{M\sigma_Y},$$

A stands for a total area surrounded by each load spot on the load-displacement curve, $A_{el(i)}$, $A_{pl(i)}$ stand for an elastic area and a plastic area corresponding to each load spot respectively, k stands for the elastic section slope on the load-displacement curve;

Step 11. calculating a nominal load $P_N$ and a nominal displacement $V_{pl}$, wherein, $$P_{N(i)} = \frac{P_i}{WB[1 - a_{b(i)}/W]^{\eta_{pl}}},$$

$$P_{N(f)} = \frac{P_f}{WB[1 - a_f/W]^{\eta_{pl}}},$$

$$C_{LL(a_i)} = \frac{1}{EB_e}\left(\frac{W+a_{b(i)}}{W-a_{b(i)}}\right)^2\left[2.1630 + 12.219\left(\frac{a_{b(i)}}{W}\right) - 20.065\left(\frac{a_{b(i)}}{W}\right)^2 - 0.9925\left(\frac{a_{b(i)}}{W}\right)^3 + 20.609\left(\frac{a_{b(i)}}{W}\right)^4 - 9.9314\left(\frac{a_{b(i)}}{W}\right)^5\right],$$

$$V_{pl(i)} = \frac{V_i - P_i C_{LL(a_i)}}{W},$$

$$C_{LL(a_f)} = \frac{1}{EB_e}\left(\frac{W+a_f}{W-a_f}\right)^2\left[2.1630 + 12.219\left(\frac{a_f}{W}\right) - 20.065\left(\frac{a_f}{W}\right)^2 - 0.9925\left(\frac{a_f}{W}\right)^3 + 20.609\left(\frac{a_f}{W}\right)^4 - 9.9314\left(\frac{a_f}{W}\right)^5\right],$$

$$V_{pl(f)} = \frac{V_f - P_f C_{LL(a_f)}}{W},$$

finally forming data pairs $(V_{pl(i)}, P_{N(i)})$ $(V_{pl(f)}, P_{N(f)})$, wherein $V_{pl(f)}$ and $P_{N(f)}$ stand for the nominal displacement and the load corresponding to the final displacement-load spot which are calculated by the final average crack length $a_f$;

Step 12. obtaining a fitted curve equation with four parameters based on the nominal load-displacement data pairs, specifically comprising removing the data pairs of the nominal plastic displacement and the nominal load corresponding to the spot which satisfy $V_{pl(i)} < 0.001$, removing the data pairs of the nominal plastic displacement and the nominal load corresponding to the spots locating in the range that after the maximum nominal load and before the final spot, plotting the remaining data pairs of the nominal plastic displacement and the nominal load and the data pair $(V_{pl(f)}, P_{N(f)})$ corresponding to the final spot in Origin software, and customizing a four-parameter equation, fitting the valid data according to the four-parameter equation on the curve, wherein the four-parameter equation is as below:

$$P_{N(i)} = \frac{a + bV_{pl(i)} + cV_{pl(i)}^2}{d + V_{pl(i)}};$$

keeping the error of the load corresponding to the final spot on the fitting curve less than 0.1% during the fitting process;

Step 13. reversely recursing load-displacement data pairs $(V_i, P_i)$ corresponding to the actual crack length $a_i$ based on the four-parameter equation;

Step 14. calculating a J_R crack extension resistance curve of the specimen based on the crack length $a_i$ and the load-displacement data pairs $(V_i, P_i)$ according to ASTM E1820, specifically comprising obtaining an elastic compliance $C_{LL(a_i)}$ corresponding to the actual crack length $a_i$, the $J_{pl(i)}$, $J_{el(i)}$, $J_i$ on the crack tip, and the crack extension length $\Delta a_i$, wherein, $$V_{pl(i)} = V_i - P_i C_{LL(a_i)},$$

$$A_{pl(i)} - A_{pl(i-1)} = \frac{[P_{(i)} + P_{(i-1)}][V_{pl(i)} - V_{pl(i-1)}]}{2},$$

$$\eta_{(i-1)} = 2.0 + 0.522 b_{(i-1)}/W,$$

$$\gamma_{(i-1)} = 1.0 + 0.76 b_{(i-1)}/W,$$

$$J_{pl(i)} = \left[ J_{pl(i-1)} + \left( \frac{\eta_{(i-1)}}{b_{(i-1)}} \right) \frac{A_{pl(i)} - A_{pl(i-1)}}{B_N} \right]$$

$$\left[ 1 - \gamma_{(i-1)} \frac{a_{(i)} - a_{(i-1)}}{b_{(i-1)}} \right],$$

$$\Delta a_i = a_i - a_0,$$

plotting the crack extension length $\Delta a_i$ and the driving force on the crack tip $J_i$ in the figure, and fitting a curve according to the power-law function $y = ax^b$ to obtain a J_R crack extension resistance curve of the structural material;

Step 15. examining the validity of the J_R crack extension resistance curve, when the data obtained meet the following requirements, the J_R crack extension resistance curve is valid:

The difference between the initial crack length $a_0^i$ and the initial average crack length $a_0$ of each spot tested by the nine-spot method is less than 0.05 B, The difference between the final crack length $a_f^i$ and the final average crack length $a_f$ of each spot tested by the nine-spot method is less than 0.05 B, the $J_i$ on the crack tip of the CT specimen is less than $J_{max}$, wherein $J_{max}=\min\{b_0\sigma_Y/10, B\sigma_Y/10\}$, the crack extension length $\Delta a_i$ of the CT specimen is less than $\Delta a_{max}$, wherein $\Delta a_{max}=0.25 b_0$;

when the data obtained do not meet the requirements above, the J_R crack extension resistance curve is invalid, then re-estimating the fracture toughness $J_{IC}$ of the material and redesigning the specimen, and repeating tests and analysis according to step1-step15 until the data obtained meet the requirements above;

Step 16. calculating passivation line, limit line and valid data area, and determining the $J_Q$ in the J_R crack extension resistance curve;

Step 17. if the thickness, the initial ligament length and the slope of the initial cracking spot of the CT specimen satisfy the formula $B > 10 J_Q/\sigma_Y$, $b_0 > 10 J_Q/\sigma_Y$ and $\Delta a = \Delta a_Q$, $dJ/da(\Delta a_Q) < \sigma_Y$ respectively, and thus $J_Q = J_{IC}$; otherwise, the $J_Q$ tested is related to the geometrical size, then re-estimating the fracture toughness $J_{IC}$ of the specimen and redesigning the specimen, and repeating tests and analysis according to step1-step17 until the $J_Q$ obtained meets the requirements, then the fracture toughness $J_{IC}$ of the material is obtained;

Step 18. calculating the fracture toughness per equivalent of the structural material $K_{IC}$, and obtaining the fracture toughness per equivalent of the structural material $K_{IC}$ according to the formula $K_{IC} = \sqrt{J_{IC} E/(1-v^2)}$.

Preferably, in step 1, preliminarily assessing the fracture behavior of the structural material through the stress-strain curve and the fracture morphology, and determining whether the material exhibits a ductile fracture behavior according to the value which is obtained by dividing the strain corresponding to the tensile strength on the stress-strain curve with the fracture strain and whether the fracture morphology of the tensile specimen exhibits obvious dimple features.

Preferably, the heating equipment is installed in an INSTRON or a MTS testing machine.

Preferably, in step 4, placing three thermocouples in the upper, middle and lower part of the furnace respectively, wherein the thermocouple in the middle part is close to the crack tip region of the specimen, and keeping heated. When the average temperature of the three thermocouples reaches the set temperature, this temperature are maintained for half an hour before the heating has finished.

In the present invention, the preferred conditions can be optionally combined based on the general knowledge in this field to obtain preferred embodiments of the present invention.

The positive effects achieved by the technical solutions in the present invention are as follows: 1. Fracture characteristics of the materials are assessed by the tensile stress-strain curve at high temperature and the fracture morphology, then the method of measurement on fracture toughness are determined, and a method of designing an effective size for the CT specimen are provided. 2. The fracture rule of the CT specimen are studied, and a way to ensure the reliability of the fracture measurement for ductile materials at high temperature are put forward which is to groove a side slot at both sides of the specimen to reduce the serious "thumb effect" arose on the specimen's surface and increase the restraint degree of the crack tip. 3. A loading process of the specimen and a rule of the elastic compliance's variation along with the extension of the crack are studied, and the elastic compliance propose to be calculated by the initial average crack length $a_0$ of the fracture of the CT specimen, a geometrical size of the specimen (W, B) and an elastic modulus E of the materials at high temperature, and the load-displacement curve is modified to exclude the errors caused by the contacts of the specimen and the fixtures, local indentation, rigidity of the fixture, piston rigidity of the testing machine etc. During the measurement process, by modifying the load-displacement curve, a difficult problem of obtaining a reliable load-displacement curve of the loaded specimen in a high-temperature furnace is effectively solved. 4. The passivation coefficient M for ferrite materials is proposed to be 2 to ensure the validity of the measurement method. The passivation coefficient M for the materials with high toughness (such as austenitic materials and nickel-based alloys) can be obtained by calculation with its parameter of mechanical performance which is obtained according to the figure. Based on the treatment, more accurate nominal load and nominal displacement corresponding to each load spot and more reliable passivation limit curve of the cracked specimen can be obtained. 5. Origin software and a specific custom four-parameter equation are employed, initial values are set for the parameters and then fit the curve for several times to ensure the validity of the final fitting curve. A weighting function is employed to ensure the accuracy of the fitting curve by increasing the weight of the final spot and keeping the error of the load corresponding to the final spot on the fitting curve less than 0.1% relative to the actual spot. 6. Several crack lengths $a_1 \ldots a_i \ldots$ are proposed to be inserted between the initial average crack length $a_0$ and the final average crack length $a_f$, then a formula is built according to the Excel sheets and the load-displacement data pairs($P_i$, $V_i$) corresponding to the crack length $a_i$ are achieved by reversely recursing. As long as the requirement of the error is met, the load-displacement data pairs ($P_i$, $V_i$) corresponding to the crack length $a_i$ are obtained. With this reverse recursion method, the calculation is more quickly and the results are more accurate.

DETAILED DESCRIPTION OF THE PREFERRED EMBODIMENT

The present invention is illustrated more clearly and completely by the following preferred embodiments and the drawings.

The method of measurement and determination on fracture toughness of structural materials at high temperature in the present invention, comprises:

Step 1. conducting a high-temperature tensile test on a standard tensile specimen of a structural material to obtain high-temperature tensile mechanical properties of the material(stress-strain curve, yield strength, tensile strength, elongation, reduction of area, strain index, etc.), and preliminarily assessing a fracture behavior of the structural material by the stress-strain curve and the fracture morphology. If the value which was obtained by dividing the strain corresponding to the tensile strength on the stress-strain curve with the fracture strain was small and the fracture morphology of the tensile specimen showed obvious dimple features, the material is determined to exhibit a ductile fracture behavior.

Figure 1:
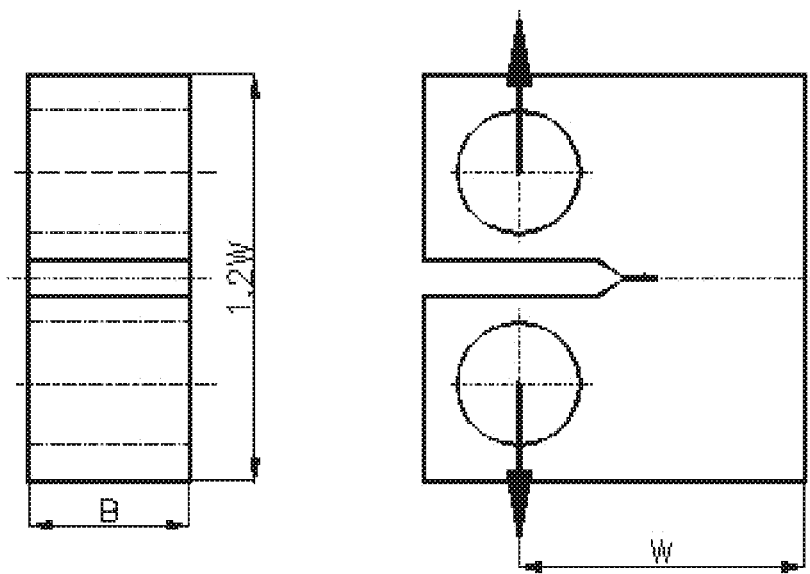
FIG. 1 demonstrates a size of a CT specimen of a preferred embodiment in the present invention.

Step 2. according to the ductile fracture behavior characteristics, the fracture of the structural material at high temperature can be described with parameters J_R crack extension resistance curve and fracture toughness $J_{IC}$. Fracture toughness $K_{IC}$ of the structural material at high temperature was pre-estimated, and $J_{IC}$ was obtained according to formula (1), and the width (W) and thickness (B) of the compact tension specimen (CT specimen) were further obtained according to formula (2), (3) and (4). The designed CT specimen was shown as FIG. 1.

$$J_{IC} = \frac{K_{IC}^2(1-\nu^2)}{E} \quad (1)$$

Wherein, E, ι stand for the elastic modulus and Poisson ratio of the material respectively.

$$W = a_0 + b_0 \geq 2 \times 10 J_{IC}/\sigma_Y \quad (2)$$

$$\sigma_Y = \frac{(\sigma_{ys} + \sigma_{uts})}{2} \quad (3)$$

Wherein, $a_0, b_0$ stand for an initial average crack length and an initial average ligament size of the CT specimen respectively, mm. $\sigma_{ys}$, $\sigma_{uts}$, stand for a yield strength and a tensile strength of the structural material respectively, MPa.

$$2 \leq W/B \leq 4 \quad (4)$$

Step 3. inducing fatigue cracks on the CT specimen through a high frequency fatigue testing machine. Then a side slot with a depth of 10% B was grooved at each side of the specimen with crack surfaces along the thickness direction according to the standard of ASTM E1820. The side slot were grooved for two main reasons: (1) increasing the restraint degree on the crack tip, eliminating or reducing "thumb effect" arose on the specimen surface; (2) the shear lip fracture mechanism on the specimen's surface having a great impact on the results of the fracture test on the ductile material, in order to obtain are liable J_R crack extension resistance curve and fracture toughness $J_{IC}$ of the structural material at high temperature, part of the surface material on the crack surface sand both sides of the specimen is required to be removed so as to reduce errors.

Step 4. measuring the size of the CT specimen (width W and thickness B) with a vernier caliper, then placing the specimen into a heating furnace equipped in a INSTRON or MTS testing machine, and placing three thermocouples in the upper, middle and lower part of the furnace respectively wherein the thermocouple placed in the middle part was close to the crack tip region of the specimen to ensure the reliability of the temperature collected. Then the furnace was closed and the heating equipment was turned on. Only if the average temperature of the upper, middle and lower thermocouples was close to and almost the set temperature, the requirement of the temperature was met. The temperature was kept for half an hour before the heating finished to ensure the harden ability of the specimen material.

Step 5. turning on the INSTRON or MTS testing machine, and monotonic loading the specimen. A load-piston displacement curve ($P_i$-$v_i$ curve) of the specimen was obtained by the load-displacement transmission device on the testing machine. During the loading process, the fracture test was observed and controlled by the load-piston displacement curve of the specimen. In order to prevent the fracture of the specimen caused by instability during a later period of the loading process, when the load of the specimen went through the maximum load point and the load fell down to approximately 90% of the maximum load, the testing machine was stopped. Then the heating equipment was turned off and the specimen was naturally cooled down.

Figure 2:
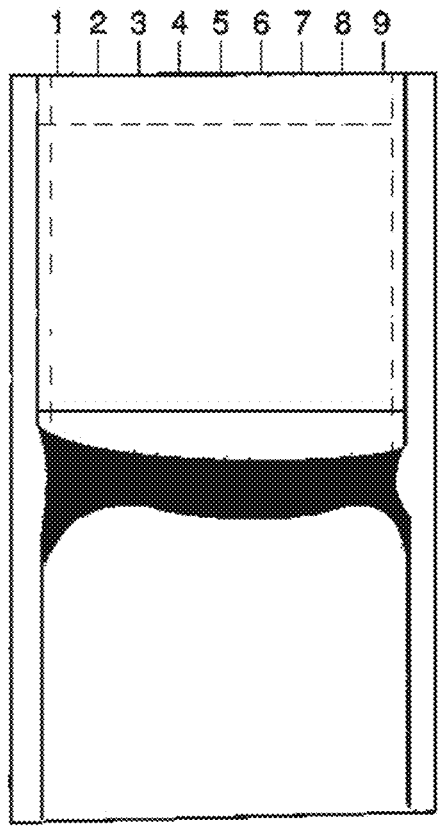
FIG. 2 demonstrates a crack length test on the fracture of a specimen of a preferred embodiment in the present invention.

Step 6. cooling the CT specimen to room temperature, opening the furnace's cavity, tensing the specimen till it was fractured with the INSTRON or MTS testing machine. As shown in FIG. 2, along the thickness direction of the specimen, a thickness of 0.01B was removed at each side of the fracture, and the remaining thickness was divided into 8 equal parts. The fracture information was observed and collected by an optical microscope or a camera, and the initial crack length $a_0^i$ and the final crack length $a_f^i$ at nine spots on the crack surface were measured. The initial average crack length $a_0$ and the final average crack length $a_f$ of the crack were obtained according to formula (5) and (6).

$$a_0 = \frac{1}{8}\left[\frac{1}{2}(a_0^1 + a_0^9) + \sum_{i=2}^{8} a_0^i\right] \quad (5)$$

$$a_f = \frac{1}{8}\left[\frac{1}{2}(a_f^1 + a_f^9) + \sum_{i=2}^{8} a_f^i\right] \quad (6)$$

Step 7. obtaining initial elastic compliance $C_{LL(a_0)}$ of the specimen according to formula (7) and (8) based on the size of the specimen ($a_0$, B, $B_N$, W) and the elasticity modulus E of the structural material at high temperature.

$$C_{LL(a_0)} = \frac{1}{EB_e}\left(\frac{W+a_0}{W-a_0}\right)^2\left[2.1630 + 12.219\left(\frac{a_0}{W}\right) - 20.065\left(\frac{a_0}{W}\right)^2 - 0.9925\left(\frac{a_0}{W}\right)^3 + 20.609\left(\frac{a_0}{W}\right)^4 - 9.9314\left(\frac{a_0}{W}\right)^5\right] \quad (7)$$

$$B_e = B - \frac{(B-B_N)^2}{B} \quad (8)$$

Wherein, $B_N$ stand for the net thickness which is achieved by deducting the depth of the slot on both sides of the CT specimen, mm.

Figure 3:
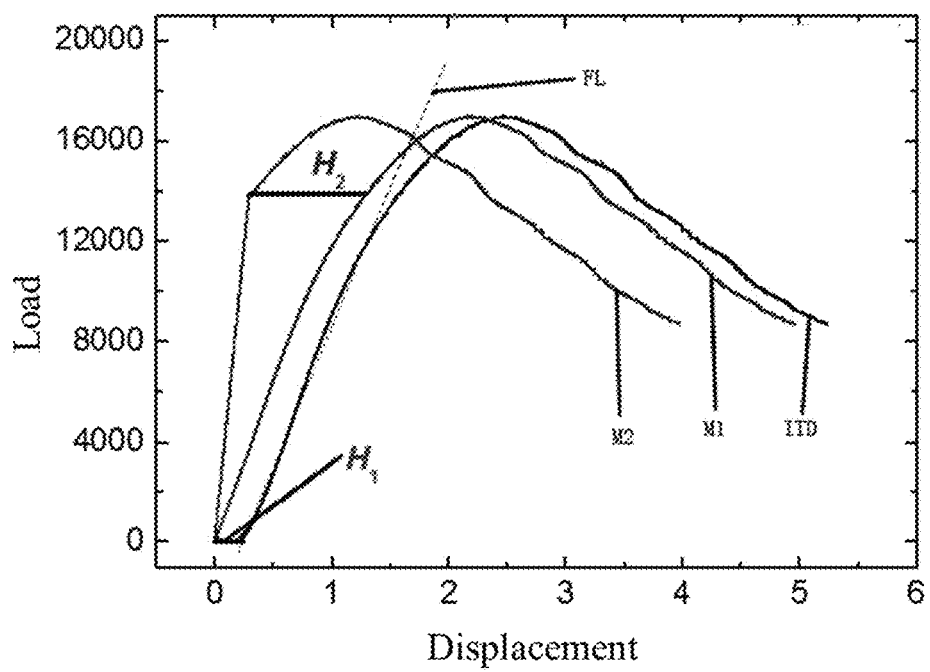
FIG. 3 is a modified load-displacement curve of a preferred embodiment in the present invention.

Step 8. modifying testing errors on the load-displacement curve caused by load contacts, local indentation, piston rigidity of the testing machine, rigidity of the fixture, etc. The modification process was conducted by two steps:

firstly, a load-displacement curve corresponding to the initial testing data (i.e. the line ITD in FIG. 3) was obtained, the errors caused by the contact of the specimen and the fixture during the loading process were removed to obtain a modified load-displacement curve (modified line 1, i.e. the line M1 in FIG. 3). Specific operation comprises: fitting the elastic line segment of the load-displacement curve (fitting line, i.e. the line FL in FIG. 3.) to obtain a linear equation y=a+bx. Assuming y=0, the equation was solved to get: x=−a/b. Then keeping the load data unchanged, all the displacement data spots minus (−a/b) resulted in a parallel movement by $H_1$ of the initial curve so as to obtain a modified line 1 (i.e. the line M1 in FIG. 3).

Secondly, the testing errors caused by the piston rigidity of the testing machine, the rigidity of the fixture, etc. were modified based on the initial elastic compliance $C_{LL(a_0)}$ to obtain a load-displacement curve (modified line 2, i.e. line M2 in FIG. 3) which can reflect the fracture process of the CT specimen. Specific operation comprises: dividing the load-displacement curve M1 (Modified line 1) into an elasticity segment and a plasticity segment and calculating the elastic slope k (k=1/$C_{LL(a_0)}$) according to $C_{LL(a_0)}$. Keep the load $P_i$ of the elasticity segment unchanged and modify the displacement corresponding to each spot of the elasticity segment according to the formula ($V_i = P_i \cdot C_{LL(a_0)}$), what is to say that the slope of the elasticity segment of line M1 in FIG. 3 was modified to be k. Since the specimen loading process was a monotonic loading process and the rigidity of the machine piston and the fixture was better than that of the specimen, the displacement difference of the specimen of the plastic segment was maintained basically constant, and hardly varied with the crack extension. According to this, the variation of the displacement corresponding to the final spot of the elasticity segment $H_2$ ($H_2 = v_i - P \cdot C_{LL(a_0)}$) was calculated, and then all the displacement of the plastic segment minus $H_2$ when the load of the modified and initial curve were maintained unchanged, the load-displacement curve (modified line 2, i.e. the line M2 in FIG. 3) which can be able to reflect the fracture process of the CT specimen was obtained.

Step 9. calculating the passivation coefficient M of the loaded crack specimen according to the mechanical properties of the material.

Figure 4:
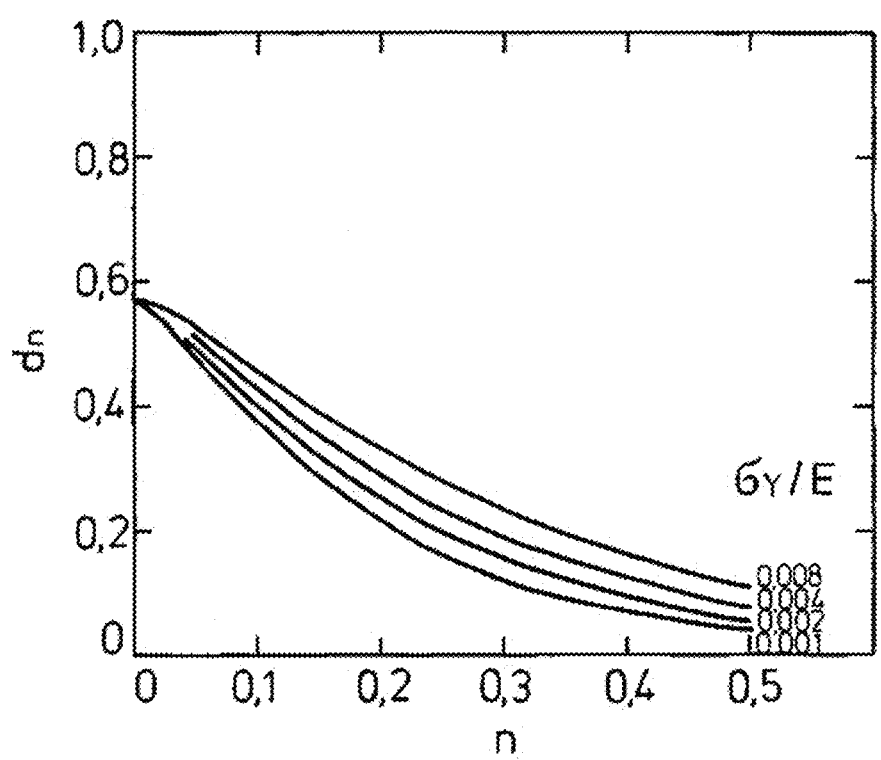
FIG. 4 is a calculation graph for passivation parameter $d_n$ of a thick specimen of a preferred embodiment in the present invention.
Figure 5:
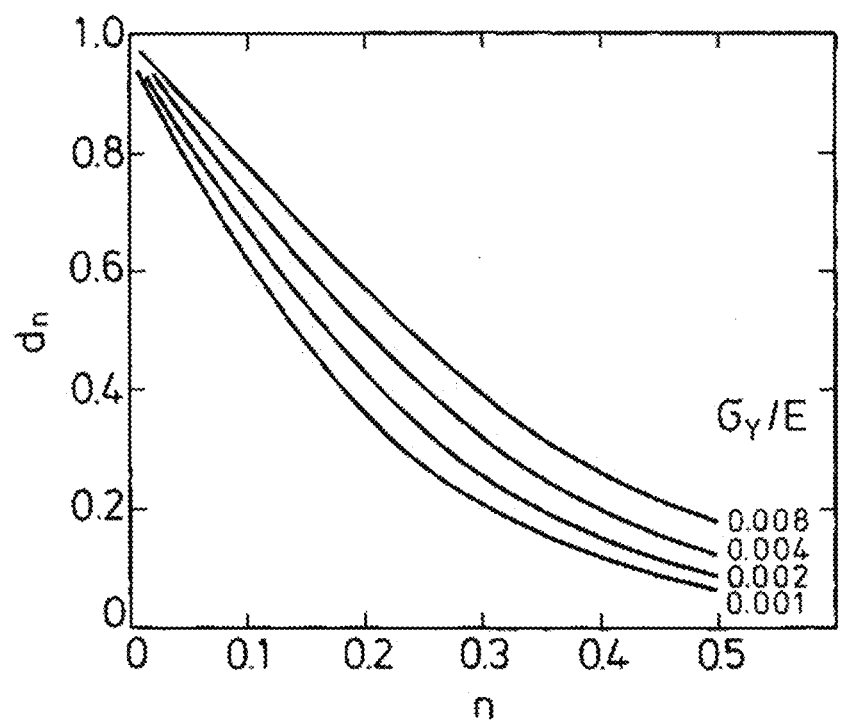
FIG. 5 is a calculation graph for passivation parameter $d_n$ of a thin specimen of a preferred embodiment in the present invention.

The passivation coefficient M for ferrite materials was proposed to be 2 usually. As for austenitic materials or nickel-based alloys with high toughness, the M was obtained according to the formula $$M = \frac{\sigma_{ys}}{0.4 d_n},$$

and in the prior arts, the passivation parameter $d_n$ was related to strain hardening coefficient n and yield strain $\sigma_{ys}/E$. The relationship of $d_n$, n and $\sigma_{ys}/E$ under plane strain and plane stress was shown in FIG. 4 and FIG. 5. As for the thick CT specimen, $d_n$ was achieved according to the coordinate system in FIG. 4. As for the thinner CT specimen, $d_n$ was achieved according to the coordinate system in FIG. 5.

Step 10. calculating the modified crack length $a_{b(i)}$ corresponding to each load spot according to formula (9)-(16) based on the modified load-displacement curve, the initial average crack length $a_0$ and the passivation coefficient M of the ductile material.

$$f\left(\frac{a_0}{W}\right) = \frac{\left[\left(2 + \frac{a_0}{W}\right)\left(0.886 + 4.64\left(\frac{a_0}{W}\right) - 13.32\left(\frac{a_0}{W}\right)^2 + 14.72\left(\frac{a_0}{W}\right)^3 - 5.6\left(\frac{a_0}{W}\right)^4\right)\right]}{\left(1 - \frac{a_0}{W}\right)^{1.5}} \quad (9)$$

$$K_{(i)} = \frac{P_i}{(BB_N W)^{0.5}} f\left(\frac{a_0}{W}\right) \quad (10)$$

$$J_{el(i)} = \frac{K_{(i)}^2 (1 - v^2)}{E} \quad (11)$$

$$A_{pl(i)} = A_i - A_{el(i)} = A_i - \frac{P_i^2}{2k} \quad (12)$$

$$\eta_{pl} = 2 + 0.522 b_0/W = 2 + 0.522(W - a_0)/W \quad (13)$$

$$J_{pl(i)} = \frac{\eta_{pl} A_{pl(i)}}{B_N b_0} \quad (14)$$

$$J_i = J_{el(i)} + J_{pl(i)} \quad (15)$$

$$a_{b(i)} = a_0 + \frac{J_i}{M \sigma_Y} \quad (16)$$

Wherein, $v$ stands for Poisson ratio of the material, $A_i$ stands for a total area surrounded by each load spot on the load-displacement curve which can be obtained by integrating with origin software, $A_{el(i)}$, $A_{pl(i)}$ stand for an elastic area and a plastic area of each load spot, k stands for the slope of the elastic segment on the load-displacement curve.

Step 11. calculating the nominal load $P_N$ and nominal displacement $V_{pl}$ according to formula (17)-(22).

The nominal load $P_N$ is:

$$P_{N(i)} = \frac{P_i}{WB[1 - a_{b(i)}/W]^{\eta_{pl}}} \quad (17)$$

The nominal load corresponding to the final load spot was calculated with the final average crack length $a_f$:

$$P_{N(f)} = \frac{P_f}{WB[1 - a_f/W]^{\eta_{pl}}} \quad (18)$$

The nominal plastic displacement is:

$$C_{LL(a_i)} = \frac{1}{EB_e}\left(\frac{W + a_{b(i)}}{W - a_{b(i)}}\right)^2 \Big[2.1630 + 12.219\left(\frac{a_{b(i)}}{W}\right) - 20.065\left(\frac{a_{b(i)}}{W}\right)^2 - 0.9925\left(\frac{a_{b(i)}}{W}\right)^3 + 20.609\left(\frac{a_{b(i)}}{W}\right)^4 - 9.9314\left(\frac{a_{b(i)}}{W}\right)^5\Big] \quad (19)$$

$$V_{pl(i)} = \frac{V_i - P_i C_{LL(a_i)}}{W} \quad (20)$$

The elastic compliance and the plastic displacement corresponding to the final crack length were obtained according to the final average crack length $a_f$ which were:

$$C_{LL(a_f)} = \frac{1}{EB_e}\left(\frac{W + a_f}{W - a_f}\right)^2 \Big[2.1360 + 12.219\left(\frac{a_f}{W}\right) - 20.065\left(\frac{a_f}{W}\right)^2 - 0.9925\left(\frac{a_f}{W}\right)^3 + 20.609\left(\frac{a_f}{W}\right)^4 - 9.9314\left(\frac{a_f}{W}\right)^5\Big] \quad (21)$$

$$V_{pl(f)} = \frac{V_f - P_f C_{LL(a_f)}}{W} \quad (22)$$

The nominal plastic displacement and the nominal load were one-to-one correspondence to form the data pairs $(V_{pl(i)}, P_{N(i)})$ $(V_{pl(f)}, P_{N(f)})$.

Step 12. obtaining a fitted curve equation with four parameters based on the nominal load-displacement data pairs.

Data pairs of the nominal plastic displacement and the nominal load which satisfied $V_{pl(i)}<0.001$ were removed, and data pairs of the nominal plastic displacement and the nominal load locating in the range that after the maximum nominal load and before the final spot were removed. The remaining data pairs of the nominal plastic displacement and the nominal load and the data pair $(V_{pl(f)}, P_{N(f)})$ corresponding to the final spot were plotted in Origin software, and a custom four-parameter equation was represented by formula (23). Then fit a curve with the above data according to the four-parameter equation:

$$P_{N(i)} = \frac{a + bV_{pl(i)} + cV_{pl(i)}^2}{d + V_{pl(i)}} \quad (23)$$

Figure 6:
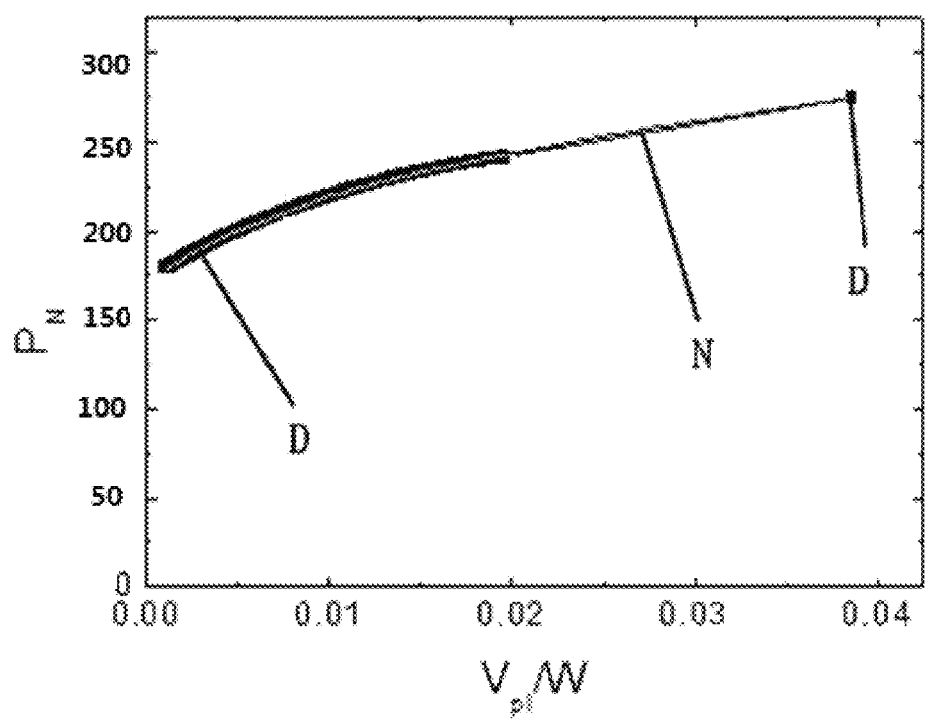
FIG. 6 is a graph of nominal load-displacement data pairs and its fitted curve of a preferred embodiment in the present invention.

While fitting the curve, the error of the load value on the fitted curve of the final spot should be kept less than 0.1% relative to the actual measured load value. In order to ensure the accuracy of the fitting, a weighting function was employed which increase the weight of the final spot so as to make the fitting meet the requirement. Detailed operation could refer to the appendix: no more tautology for the method of weight function fitting with details herein. The nominal load-displacement data pairs and the fitting curve were shown in FIG. 6, which included discrete data spots D and a fitted curve N. The data spots D were fitted in the curve N, thus, the fitted curve equation could be obtained therewith. Herein, the FIG. 6 was only an illustration of an embodiment, the figure will vary when the specific experimental data are different.

Step 13. obtaining the load-displacement data pairs $(V_i, P_i)$ corresponding to the actual crack length $a_i$ by reverse recursion based on the four-parameter equation. The method comprises: firstly, taking several crack lengths $a_1, a_2, a_3 \ldots a_i$ between the initial average crack length $a_0$ and the final average crack length $a_f$, then Table columns of crack length, elastic compliance, nominal displacement, nominal load, fitted load, (fitted load-nominal load)/nominal load were constructed following the column of load and displacement in excel sheet as shown in Table A. When the final average crack length reached $a_f$ (which is 18.1305 in Table A), the elastic compliance was obtained according to formula (21), and the nominal displacement, the nominal load, the fitted load corresponding to the final displacement, the final load, the final crack length were obtained according to formula (22), (18) and (23) respectively. If [(the fitted load−the nominal load)/the nominal load]<0.001, the final crack length $a_f$ was recognized in correspondence with the final displacement-load data pair $(v_f, P_f)$ ((3.03579, 14361.8) in Table A). When the crack length was adjusted to $a_i$ (which was 18 in Table A), the $a_{b(i)}$ in formula (19) was replaced with $a_i$ to calculate the corresponding elastic compliance. Then the nominal displacement, the nominal load, the fitted load corresponding to the displacement, the load, the crack length in the corresponding rows of the excel sheet were obtained according to formula (20), (17) and (23). If ((the fitted load−the nominal load)/the nominal load)>0.001, it was proved that the displacement-load data pair in the row of the excel sheet was not in correspondence with the instant crack length $a_i$. Then, the data were continued to be reversely recursed along the arrow direction in Table A. When ((the fitted load−the nominal load)/the nominal load)<0.001 (which is 1.81545E−05 in Table A), it was considered that the displacement-load data pair $(v_i, P_i)$ (2.95579, 14629.3) in Table A) in the row was in correspondence with the instant crack length $a_i$. Similarly, the crack length was adjusted to $a_{i-1}$, the displacement-load data pair $(V_{i-1}, P_{i-1})$ corresponding to the crack length $a_{i-1}$ was obtained according to the above recursion. The reverse recursion was repeated in a such way until the displacement-load data pair $(V_0, P_0)$ corresponding to the initial average crack length $a_0$ was obtained.

(28). The $a_0$ in formula (9), (10) was replaced with the actual crack length $a_i$ and the $J_{el(i)}$ was obtained according to formula (11). Then $J_i$ on the crack tip was obtained according to formula (15), and the crack extension length $\Delta a_i$ was obtained according to formula (29).

$$V_{pl(i)} = V_i - P_i C_{LL(a_i)} \qquad (24)$$

$$A_{pl(i)} - A_{pl(i-1)} = \frac{[P_{(i)} + P_{(i-1)}][V_{pl(i)} - V_{pl(i-1)}]}{2} \qquad (25)$$

$$\eta_{(i-1)} = 2.0 + 0.522 b_{(i-1)}/W \qquad (26)$$

$$\gamma_{(i-1)} = 1.0 + 0.76 b_{(i-1)}/W \qquad (27)$$

$$J_{pl(i)} = \left[J_{pl(i-1)} + \left(\frac{\eta_{(i-1)}}{b_{(i-1)}}\right)\frac{A_{pl(i)} - A_{pl(i-1)}}{B_N}\right]\left[1 - \gamma_{(i-1)}\frac{a_{(i)} - a_{(i-1)}}{b_{(i-1)}}\right] \qquad (28)$$

$$\Delta a_i = a_i - a_0 \qquad (29)$$

The crack extension length $\Delta a_i$ and the driving force $J_i$ on the crack tip were plotted in the figure, and the J_R crack extension resistance curve of the structural material was obtained by fitting a curve according to the power-law function $y=ax^b$.

Step 15. examining the validity of the J_R crack extension resistance curve.

The J_R crack extension resistance curve was valid when the data obtained met the following requirements:

TABLE A

Reverse recurse the displacement-load data pair corresponding to the crack length

| Displacement | Load | Crack Length | Elastic compliance | Nominal Displacement | Nominal Load | Fitted Load | (Fitted load-Nominal Load)/Nominal Load | Remark |
|---|---|---|---|---|---|---|---|---|
| 2.95579 | 14629.3 | 18 | 2.946E−05 | 0.084021947 | 254.5638307 | 254.5684522 | 1.81545E−025 | The second set of recursion data ↑ |
| ... | ... | ... | ... | ... | ... | ... | ... | |
| ... | ... | ... | ... | ... | ... | ... | ... | |
| 3.03034 | 14403.27 | 18 | ... | ... | ... | ... | ... | |
| 3.03046 | 14396.61 | 18 | ... | ... | ... | ... | ... | |
| 3.03047 | 14409.71 | 18 | ... | ... | ... | ... | ... | |
| 3.03232 | 14391.17 | 18 | ... | ... | ... | ... | ... | |
| 3.03199 | 14416.23 | 18 | ... | ... | ... | ... | ... | |
| 3.03229 | 14384.47 | 18 | ... | ... | ... | ... | ... | |
| 3.03143 | 14407.23 | 18 | ... | ... | ... | ... | ... | |
| 3.0333 | 14389.5 | 18 | ... | ... | ... | ... | ... | |
| 3.03383 | 14406.13 | 18 | ... | ... | ... | ... | ... | |
| 3.03438 | 14396.97 | 18 | 2.94567E−05 | 0.086864998 | 250.5210662 | 256.1949507 | 0.022648333 | |
| 3.03499 | 14392.02 | 18 | 2.94567E−05 | 0.086890149 | 250.4349315 | 256.2093271 | 0.023057469 | |
| 3.03348 | 14398.48 | 18 | 2.94567E−05 | 0.086833567 | 250.5473417 | 256.1769851 | 0.02246938 | |
| 3.03589 | 14377.98 | 18 | 2.94567E−05 | 0.0868633862 | 250.190622 | 256.2343125 | 0.024156343 | |
| 3.03403 | 14390.47 | 18 | 2.94567E−05 | 0.086859722 | 250.40796 | 256.1919351 | 0.023098208 | |
| 3.03579 | 14361.8 | 18.1305 | 3.02172E−05 | 0.086582894 | 256.1085888 | 256.0336879 | −0.000292458 | The first set of recursion data (final) |

Step 14. calculating the J_R crack extension resistance curve of the specimen based on the crack length $a_i$ and the displacement-load data pairs $(V_i, P_i)$ according to ASTM E1820. The $a_{b(i)}$ was replaced with the actual crack length $a_i$ according to formula (19) to obtain the elastic compliance $C_{LL(a_i)}$ corresponding to the actual crack length $a_i$. The $J_{pl(i)}$ was obtained according to formula (24), (25), (26), (27), The difference between the initial crack length $a_0^i$ and the initial average crack length $a_0$ of each spot tested by the nine-spot method was less than 0.05 B The difference between the final crack length $a_f^i$ and the final average crack length $a_f$ of each spot tested by the nine-spot method was less than 0.05 B The temperature, the fixture the testing equipment error and the loading rate, etc. met the requirements of the test during the testing process.

The $J_i$ on the crack tip of the CT specimen was less than $J_{max}$, wherein the $J_{max}$ was obtained according to formula (30).

$$J_{max}=\min\{b_0\sigma_Y/10, B\sigma_Y/10\} \quad (30)$$

The crack extension length $\Delta a_i$ of the CT specimen was less than $\Delta a_{max}$, wherein the $\Delta a_{max}$ was obtained according to formula (31).

$$\Delta a_{max}=0.25 b_0 \quad (31)$$

If the data obtained did not meet the requirements above, the fracture toughness of the structural material should be re-estimated and the specimen size should be redesigned. Repeat the tests and analysis according to step1-step15 until the data obtained met the requirements above.

Step 16. calculating a passivation line, a limit line and a valid data area.

The passivation line, 0.15 mm passivation bias line, 0.20 mm passivation bias line, 1.5 mm passivation bias line, $J_{limit}$ line of the CT specimen's crack were obtained according to formula (32), (33), (34), (35), (36) respectively. $\Delta a_{min}$ and $\Delta a_{limit}$ were the abscissa corresponding to the intersection of the 0.15 mm passivation bias line and the J_R crack extension resistance curve and the intersection of the 1.5 mm passivation bias line and the J_R crack extension resistance curve respectively. M was obtained according to step 9.

$$J=M\sigma_Y\Delta a \quad (32)$$

$$J=M\sigma_Y(\Delta a-0.15) \quad (33)$$

$$J=M\sigma_Y(\Delta a-0.20) \quad (34)$$

$$J=M\sigma Y(\Delta a-1.5) \quad (35)$$

$$J_{limit}=b_0\sigma_Y/7.5 \quad (36)$$

Figure 7:
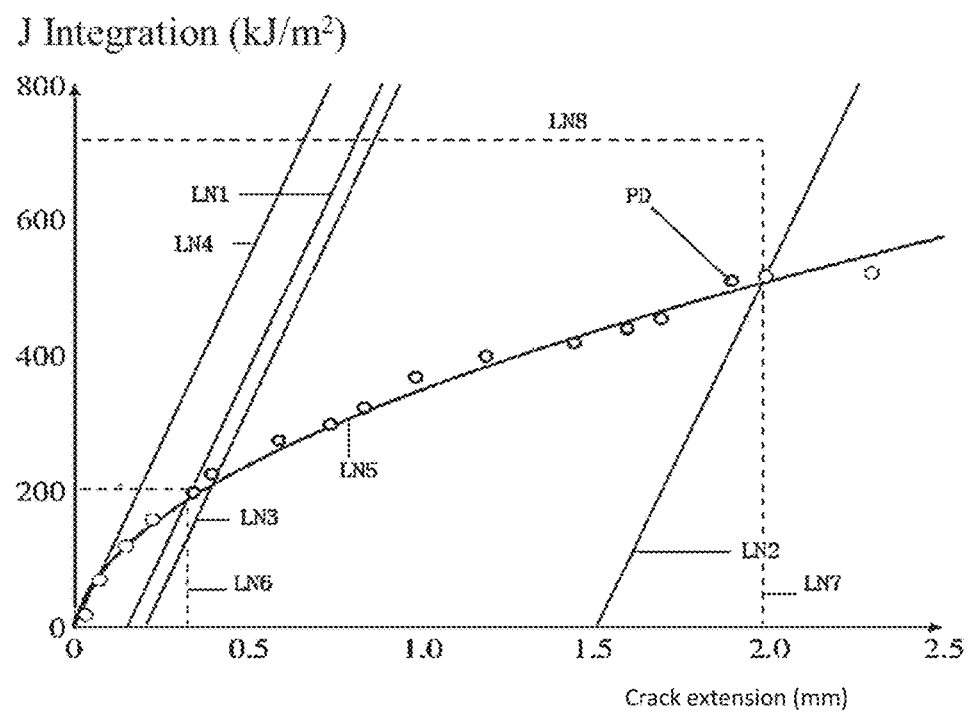
FIG. 7 is a graph of the crack extension resistance curve and its limited scope of a preferred embodiment in the present invention.

The $J_{limit}$ line (line LN8 in FIG. 7), the $\Delta a_{min}$ line (line LN6 in FIG. 7), the $\Delta a_{limit}$ line (line LN7 in FIG. 7), the passivation line (line LN4 in FIG. 7), the 0.15 mm passivation bias line (line LN1 in FIG. 7), the 0.20 mm passivation bias line (line LN3 in FIG. 7), the 1.5 mm passivation bias line (line LN2 in FIG. 7) of the CT specimen were shown in FIG. 7. Wherein, the PD data spots located in the area surrounded by the 1.5 mm passivation bias line, the $J_{limit}$ line and the $\Delta a_{min}$ line were recognized to be valid. The abscissa corresponding to the intersection of the 0.20 mm passivation bias line and the J_R crack extension resistance curve was defined as $J_Q$.

Step 17. examining whether the $J_Q$ obtained was the fracture toughness $J_{IC}$.

If the thickness, the initial ligament length, the slope corresponding to the initial spot on the J_R crack extension resistance curve of the CT specimen fitted formula (37), (38), (39) respectively, $J_Q=J_{IC}$. Otherwise, the $J_Q$ tested was related to the geometrical size. Then re-estimate the fracture toughness $J_{IC}$ of the specimen and re-design the specimen. Repeat the tests and analysis according to step1-step17 until the obtained $J_Q$ met the requirement, the fracture toughness $J_{IC}$ of the material was obtained therewith.

$$B>10J_Q/\sigma_Y \quad (37)$$

$$b_0>10J_Q/\sigma_Y \quad (38)$$

When $\Delta a=\Delta a_Q, dJ/da(\Delta a_Q)<\sigma_Y \quad (39)$

Step 18. calculating the fracture toughness per equivalent of the structural material $K_{JC}$. The fracture toughness per equivalent of the structural material $\overline{K_{JC}}$ was obtained according to the formula $K_{JC}=\sqrt{J_{IC}E/(1-v^2)}$.

The distinguishing features of the present invention are as below:

1. Assessing the fracture characteristics of a material by a tensile stress-strain curve and the fracture morphology at high temperature, then determining a method of testing on fracture toughness, and providing a method of designing an effective size for a CT specimen.

2. Studying the fracture rule of the CT specimen, and putting forward a way to ensure the reliability of the fracture test for ductile material at high temperature which is to groove a side slot at both sides of the specimen to reduce serious "thumb effect" arose on the specimen's surface and increasing the restraint degree on the crack tip.

3. Studying the loading process of the specimen and the rule of the elastic compliance's variation along with the crack extension, and proposing to calculate the elastic compliance with the initial average crack length $a_0$ of the fracture of the CT specimen, the geometrical size of the specimen (W, B) and the elastic modulus E of the material at high temperature, and modifying the load-displacement curve to exclude the errors caused by load contacts, local indentation, rigidity of the fixture, piston rigidity of the testing machine etc during the testing process. By modifying the load-displacement curve, a difficult problem of obtaining a reliable load-displacement curve of the loaded specimen in a high-temperature furnace is effectively solved.

4. Proposing that the passivation coefficient M for the ferrite material should be 2 to ensure the validity of the testing method. The passivation coefficient M for the material with high toughness (such as austenitic materials and nickel-based alloys) is obtained by calculation with its parameters of mechanical performance obtained according to the FIG. 4 and FIG. 5. Based on this, more accurate nominal load and nominal displacement corresponding to each load spot can be obtained and more reliable passivation limit curve of the specimen with cracks can be obtained.

5. In order to ensure the validity of the final fitting, Origin software and a specific custom four-parameter equation are proposed to be employed, and initial values are set for the parameters to fit the curve. A weighting function is proposed to be employed to ensure the accuracy of the fitting for the final spot by increasing the weight of the final spot and keeping the error of the load corresponding to the final spot on the fitting curve less than 0.1% relative to the actual spot.

6. Several crack lengths $a_1 \ldots a_i \ldots$ are inserted between the initial average crack length $a_0$ and the final average crack length $a_f$, then a formula is built according to the Excel sheets and reversely recurse according to the formula. The load-displacement data pairs $(P_i, V_i)$ corresponding to the crack length $a_i$ are obtained as long as the requirement of the error is met. This method is more quickly and the results are more accurate.

A specific example in practice is as follows:

(1) Basic Description

A material is widely used in the manufacturing of a certain structure of the plant equipment in a thermal power station. The structure usually works at 500° C. It's of great significance to determine the fracture toughness of the structural material at the operating temperature for the damage tolerance design of the structure of the power station equipment, the integrity evaluation, the safety estimation for the use of the components and the residual strength analysis for the components, etc.

(2) Fracture Toughness Test of the Structural Material

Figure 8:
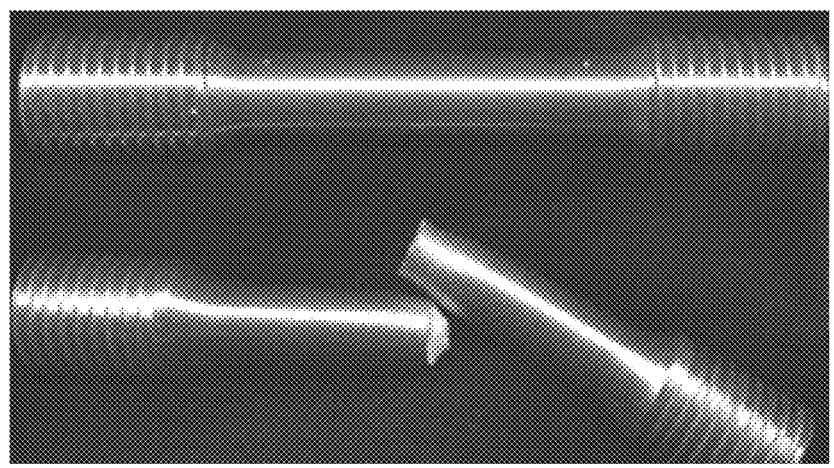
FIG. 8 is a photo for a tensile specimen of a structural material and its fracture at 500° C. of a preferred embodiment in the present invention.

Step 1. Taking a standard tensile specimen of the structural material along the direction of the crack extension tested. A quasi-static tensile test was carried on at 500° C., and the initial tensile specimen and the cracked specimen were shown in FIG. 8. The tensile mechanical properties of the material at 500° C. were shown in Table 1. According to the FIG. 8, the fracture was a cup-cone fracture. Table 2 showed that the yield strength of the material was small, the elongation and the percentage reduction of area were larger, and the value obtained from dividing the strain corresponding to the tensile strength on the stress-strain curve with the fracture strain was smaller. The fracture morphology was observed by a scanning electron microscope and the fracture of the material was found to exhibit dimple features. From all the above characteristics, the fracture of the material was determined to exhibit a ductile fracture behavior.

TABLE 1

Mechanical properties of a certain structural material

| Temperature (° C.) | $\sigma_{ys}$ (MPa) | $\sigma_{uts}$ (MPa) | $\delta$ (%) | $\psi$ (%) | E (Gpa) | $\varepsilon_{uts}/\varepsilon_f$ |
|---|---|---|---|---|---|---|
| 500 | 392.1 | 455.0 | 26.4 | 70 | 148.12 | 0.116 |

Step 2. preliminarily assessing the fracture toughness $K_{IC}$ of the material at 500° C. at about 300 Mpa·$\sqrt{m}$, and the fracture toughness $J_{IC}$ of the material was obtained according to formula (1). The width (W) and thickness (B) characterizing the CT specimen size were obtained according to formula (2), (3), (4) which were shown in Table 2. To facilitate processing and testing the specimen, the width (W) of the specimen was set to be 30 mm and the thickness (B) was set to be 15 mm at 500° C. The designed specimen size was shown in FIG. 9.

TABLE 2

Fracture toughness of a certain structural material and an estimated size of the specimen

| Temperature (° C.) | $J_{IC}$ (kJ/m²) | W (mm) | B (mm) |
|---|---|---|---|
| 500 | 552.93 | ≥26.10 | ≥6.525~13.05 |

Figure 9:
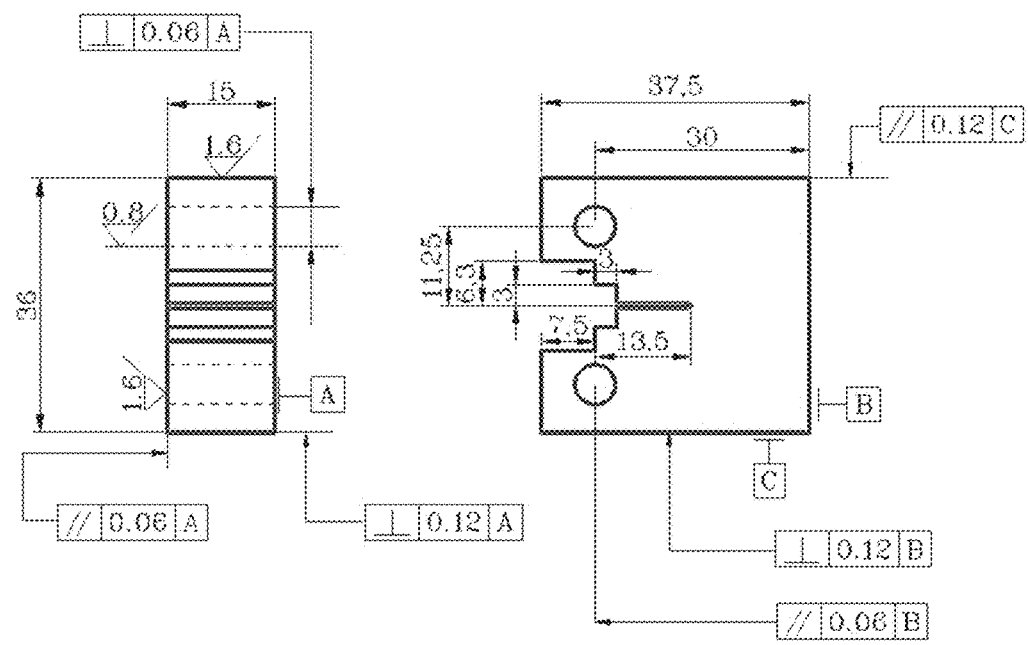
FIG. 9 demonstrates a CT specimen of a structural material at 500° C. of a preferred embodiment in the present invention.

Step 3. processing the specimen according to the FIG. 9 by a mechanical processing method. A sharp fatigue crack with a length of 1.5 mm on the crack tip of the specimen was induced through a high frequency fatigue testing machine. Then a side slot with a depth of 10% B was grooved at both sides of the specimen along the crack surface of the CT specimen according to the ASTM E1820 standard so as to increase the restraint degree on the crack tip and reduce the testing error caused by surface shear effect.

Step 4. measuring the basic size of the CT specimen by a vernier caliper which was shown in Table 3, then loading the specimen into the fixture of the INSTRON testing machine and closing the furnace. Three thermocouples were placed in the upper, middle and lower part of the furnace. Then the heating equipment was turned on. When the average value of the upper, middle and lower thermocouples was close to and almost the set temperature, the temperature in the furnace met the requirement and was stable. The specimen was kept at this temperature for half an hour to ensure a uniform distribution of the temperature inside the CT specimen.

TABLE 3

Basic size of the CT specimen

| Testing temperature (° C.) | B | $B_N$ | W |
|---|---|---|---|
| 500 | 14.95 | 12.135 | 30.05 |

Step 5. turning on the INSTRON testing machine and conducting a monotonic tensile test on the specimen. The speed rate of the piston was set to be 0.05 mm/min to ensure testing a quasi-static loading process. During the loading process, the load-displacement curve of the specimen was obtained based on the piston force and the piston displacement. The load-displacement curve of the structural material exhibited non-linear variation at 500° C. When the loading went through the maximum load spot and fell down to approximately 90% of the maximum load spot, the tensile test was stopped, the heating equipment was turned off and the specimen was naturally cooled down.

Step 6. opening the furnace after the temperature of its cavity was cooled to room temperature, then tensing the specimen till it was fractured through the INSTRON testing machine. Since the metal on the crack surface tended to be oxidized during the high-temperature testing process, the tested crack surface exhibited a certain depth of the color, which was facilitated to identify and read the information of the beginning of cracking and the crack's extension. The crack size at nine spots was obtained through an optical microscope and a nine-spot weighted average method was adopted, then the initial average crack length $a_0$ and the final average crack length $a_f$ were obtained according to formula (5) and (6). The tested crack sizes were shown in Table 4.

TABLE 4

Crack size of the specimen fracture

| Temperature | $a_0$ (mm) | $a_f$ (mm) | $\Delta a$ (mm) |
|---|---|---|---|
| 500° C. | 15.639 | 18.131 | 2.491 |

Step 7. calculating the initial elastic compliance C % of the CT specimen according to compliance formula (7) and (8) based on the size of the specimen and the crack (B, $B_N$, W, $a_0$) and the elasticity modulus E of the structural material at 500° C.

Figure 10:
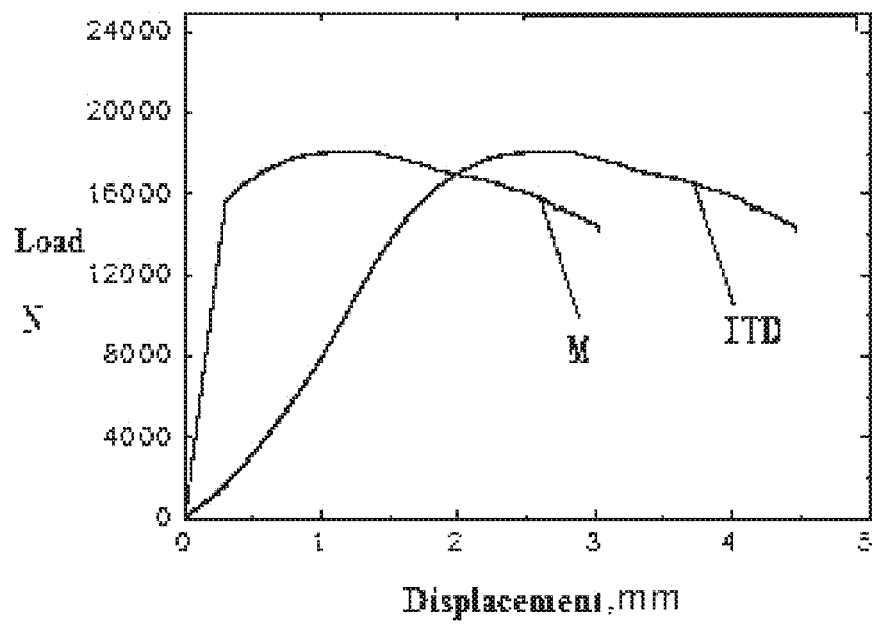
FIG. 10 is a modified load-displacement curve of a CT specimen of a structural material of a preferred embodiment in the present invention.

Step 8. modifying the testing errors caused by load contacts, local indentation, piston rigidity of the testing machine, rigidity of the fixture, etc. respectively according to the modified load-displacement curve in FIG. 3. The initial load-displacement curve ITD and the modified load-displacement curve M at 500° C. were shown in FIG. 10.

Step 9. according to the magnetic characteristics of the structural material and the microstructure pictures of the metallographic structure, the material was a ferrite material, therefore, the passivation coefficient M of the crack was 2.

Step 10. calculating a modified crack length $a_{b(i)}$ corresponding to each load spot of the CT specimen based on the initial average crack length $a_0$ of the CT specimen according to formula (9)-(16).

Step 11. calculating a nominal load $P_{N(i)}$, $P_{N(f)}$ and a nominal plastic displacement $V_{pl(i)}$, $V_{pl(f)}$ corresponding to each load spot of the CT specimen at 500° C. according to formula (17)-(22).

Figure 11:
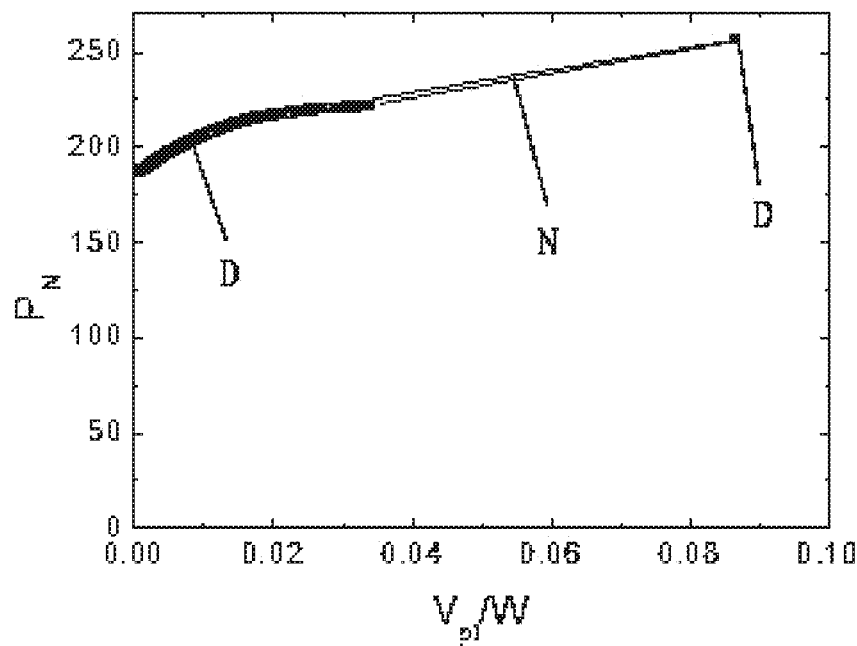
FIG. 11 is a graph of effective nominal plastic displacement and load data pairs of a structural material of a preferred embodiment in the present invention and its fitted curve at 500° C.

Step 12. removing the data pairs of the nominal plastic displacement and the nominal load which satisfy $V_{pl(i)}$<00.001, and the data pairs of the nominal plastic displacement and the nominal load locating in the range that after the maximum nominal load and before the final spot were removed. The remaining data pairs of the nominal plastic displacement and the nominal load and the data pair $(V_{pl(f)}, P_{N(f)})$ corresponding to the final spot were plotted in the Origin software, and a four-parameter equation was customized as shown in formula (23). In order to ensure the accuracy of the fitting of the final spot, the weight of the final spot was increased. Then with the valid data, a curve was fitted according to the four-parameter equation. The curve-fitting equation was fitted with the effective data pairs of the nominal plastic displacement and load of the CT specimen and the curve was shown in FIG. 11. FIG. 11 showed discrete data spots D and the fitted curve N. The curve N was fitted with the data spots D, therefore, the curve-fitting equation could be obtained therewith, i.e. y=(0.7089+211.5297x+556.05344x$^2$)/(0.004+x).

Step 13. inserting 13 crack lengths between the initial average crack length $a_0$ (15.639 mm) and the final average crack length $a_f$ (18.131 mm). The actual crack length $a_i$ corresponding to the displacement-load data pair $(V_i, P_i)$ was gradually obtained according to the four-parameter equation in FIG. 11 by the reverse recursion method described in Table A, the results of which were shown in Table 5.

TABLE 5

The corresponding relationship between displacement-load data pairs and the crack length

| No. | $V_i$ | $P_i$ | $a_i$ |
| --- | --- | --- | --- |
| 1 | 0.35107 | 16030.7 | 15.639 |
| 2 | 0.40216 | 16352.4 | 15.7 |
| 3 | 0.95521 | 18025 | 15.8 |
| 4 | 1.3005 | 18093.9 | 16 |
| 5 | 1.51534 | 17865.7 | 16.2 |
| 6 | 1.69962 | 17570.9 | 16.4 |
| 7 | 1.8509 | 17212.6 | 16.6 |
| 8 | 2.04964 | 16914.5 | 16.8 |
| 9 | 2.2549 | 16612.3 | 17 |
| 10 | 2.40743 | 16231.3 | 17.2 |
| 11 | 2.58559 | 15881.8 | 17.4 |
| 12 | 2.69497 | 15444.6 | 17.6 |
| 13 | 2.83086 | 15045.9 | 17.8 |
| 14 | 2.95579 | 14629.3 | 18 |
| 15 | 3.03579 | 14361.8 | 18.131 |

Figure 12:
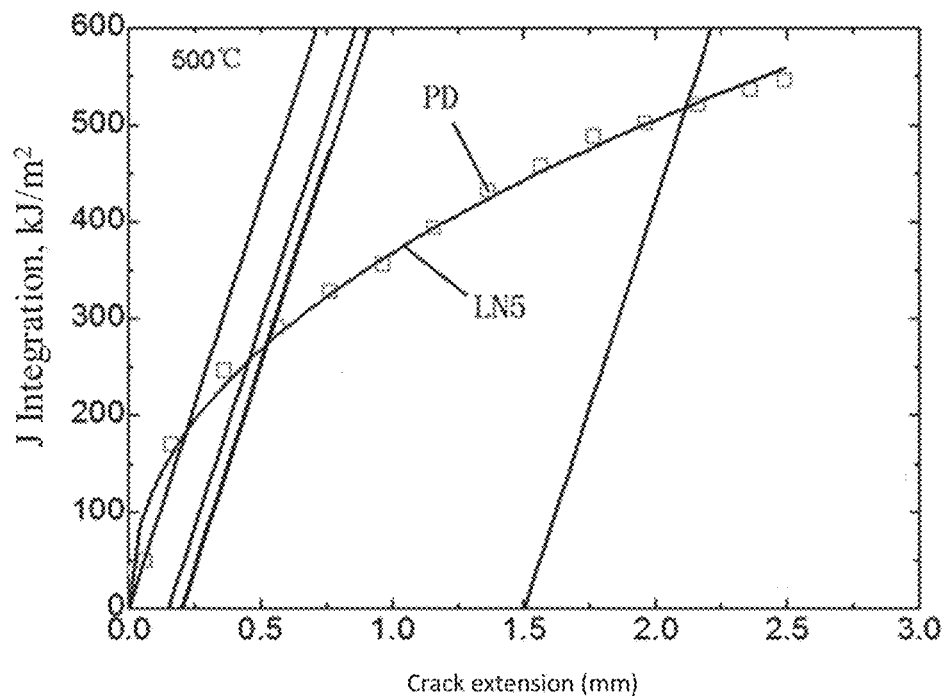
FIG. 12 is a J_R crack extension resistance curve of a structural material at 500° C. of a preferred embodiment in the present invention.

Step 14. replacing $a_{b(i)}$ with the actual crack length $a_i$ in Table 5 in formula (19) to obtain the elastic compliance $C_{LL(a_i)}$; corresponding to the actual crack length $a_i$. The $J_{pl(i)}$ was obtained according to formula (24), (25), (26), (27), (28) with the displacement and load data. The $a_0$ in formula (9), (10) was replaced with the actual crack length $a_i$ and the $J_{el(i)}$ was obtained according to formula (11). Then the $J_i$ on the crack tip was obtained according to formula (15), and the crack extension length $\Delta a_i$ was obtained according to formula (29). The crack extension length $\Delta a_i$ and the driving force $J_i$ on the crack tip were plotted in the figure, and the data spots PD were fitted according to the power-law function y=ax$^b$ to obtain the J_R crack extension resistance curve LN5 of the structural material which was shown in FIG. 12.

Step 15. examining that the difference between the initial crack length $a_0^i$ and the initial average crack length $a_0$ of each spot of the specimen fracture was less than 0.05 B. The difference between the final crack length $a_f^i$ and the final average crack length $a_f$ of each spot was less than 0.05 B. The temperature, the fixture, the testing equipment error, the loading rate, etc. met the testing requirements during the testing process.

$$J_{max}=\min[b_0\sigma_Y/10, B\sigma_Y/10]=\min[610.359, 633.207]=610.359 \text{ kJ/m}^2$$

By examination, the driving force $J_i$ of the CT specimen was less than $J_{max}$ during the testing process.

$$\Delta a_{max}=0.25b_0=3.603 \text{ mm}$$

The actual maximum crack extension length $\Delta a$=2.491 mm which was less than $\Delta a_{max}$ met the testing requirements.

In conclusion, the J_R crack extension resistance curve obtained by fracture testing was valid.

Step 16. calculating the relevant linear equation and valid data area.

The passivation line equation: $J=2\sigma_Y\Delta a=2\times423.55\Delta a=847.1\Delta a$ The 0.15 mm passivation bias line equation: $J=2\sigma_Y(\Delta a-0.15)=847.1(\Delta a-0.15)$ The 0.2 mm passivation bias line equation: $J=2\sigma_Y(\Delta a-0.2)=847.1(\Delta a-0.2)$ The 1.5 mm passivation bias line: $J=2\sigma Y(\Delta a-1.5)=847.1(\Delta a-1.5)$ The $J_{limit}$ line: $J_{limit}=b_0\sigma_Y/7.5=813.84 \text{ kJ/m}^2$ The passivation line, the 0.15 mm passivation bias line, the 0.2 mm passivation bias line and the 1.5 mm passivation bias line were shown in FIG. 13. Wherein, the abscissa corresponding to the intersection of the 0.15 mm passivation bias line and the J_R crack extension resistance curve was $\Delta a_{min}$, the abscissa corresponding to the intersection of the 1.5 mm passivation bias line and the J_R crack extension resistance curve was $\Delta a_{limit}$. The spot data which satisfied $\Delta a_{min}<\Delta a<\Delta a_{limit}$ and $J_i<J_{limit}$ were valid data during the testing process. The ordinate corresponding to the intersection of the 0.20 mm passivation bias line and the J_R crack extension resistance curve was $J_Q$, the value of which was 273.817 kJ/m$^2$ and shown in FIG. 12.

Step 17. examining whether $J_Q$ obtained was the fracture toughness $J_{IC}$. $10J_Q/\sigma_Y=6.465$ mm For the CT specimen, B=14.95 mm, $b_0$=14.411 mm, which met the requirement of B, $b_0>10J_Q/\sigma_Y$.

Figure 13:
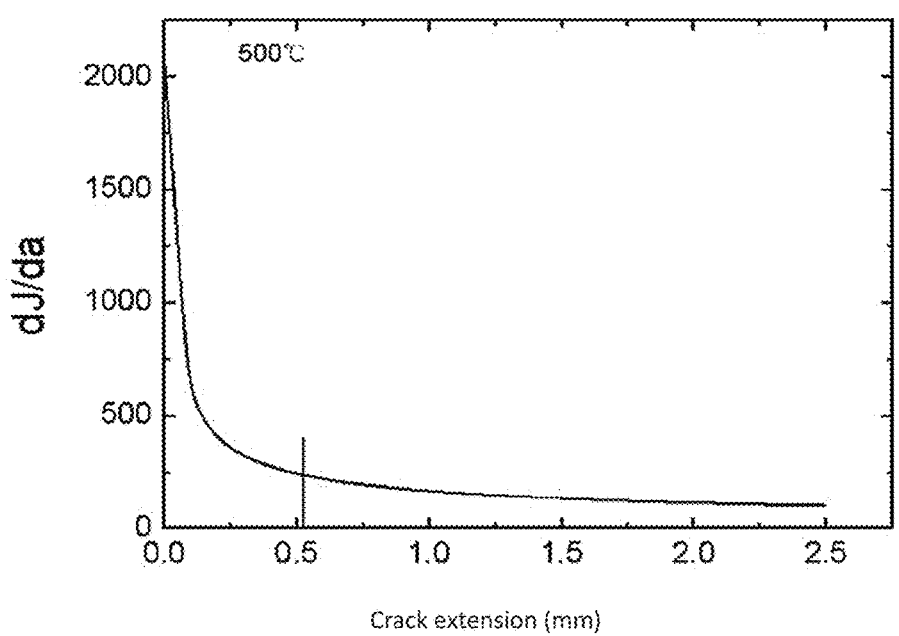
FIG. 13 is a slope verification graph of a crack extension resistance curve of a preferred embodiment in the present invention.

The slope verification graph of the J_R crack extension resistance curve was shown as FIG. 13. When $\Delta a=\Delta a_Q$, dJ/da=240.008 and $\sigma_Y$=423.55, the requirement of dJ/da<$\sigma_Y$ was met.

In conclusion, $J_Q=J_{IC}$=273.817 kJ/m$^2$ was obtained.

Step 18. calculating the fracture toughness per equivalent of the structural material $K_{IC}$.

$$K_{IC}=\sqrt{J_{IC}E/(1-v^2)}=\sqrt{273.817\times148120/[(1-0.3^2)\times1000]}=211.114 \text{ Mpa}\sqrt{m}.$$

Appendix: Weight Function Fitting Method

Illustrate Origin 8.0 software as an example, the fitting was conducted according to the following steps:

Step 1: To make the fitted curve go through the key spot (the final spot), a higher weight should be set on the key spot. As shown in Table 6, the weight of the final spot was set to be 5000, while the others were set to be 1.

TABLE 6

Data fitting Table based on the weight setting

| Row A Displacement | Row B Load | Row C Weight | Remarks |
|---|---|---|---|
| 0.00103 | 145.6836 | 1 | |
| 0.00107 | 145.6376 | 1 | |
| 0.00103 | 145.765 | 1 | |
| 0.00103 | 145.7311 | 1 | |
| 0.00104 | 145.7615 | 1 | |
| 0.00108 | 145.8253 | 1 | |
| 0.00111 | 145.752 | 1 | |
| ... | ... | 1 | |
| ... | ... | 1 | |
| 0.09138 | 177.312 | 1 | |
| 0.0914 | 176.8257 | 1 | |
| 0.09137 | 177.3283 | 1 | |
| 0.09138 | 177.0189 | 1 | |
| 0.09142 | 177.1377 | 1 | |
| 0.09139 | 177.0759 | 1 | |
| 0.09141 | 177.028 | 1 | |
| 0.09141 | 177.2469 | 1 | |
| 0.09146 | 176.9173 | 1 | |
| 0.09144 | 177.4465 | 1 | |
| 0.15784 | 177.84 | 5000 | The final spot |

Step 2: a fitted function was customized in Origin 8.0: Analysis_Fitting_Nonlinear Curve Fit_Open Dialog, then the fitted function was defined in the dialog box at first:

$y=(a+bx+cx^2)/(d+x)$

Figure 14:
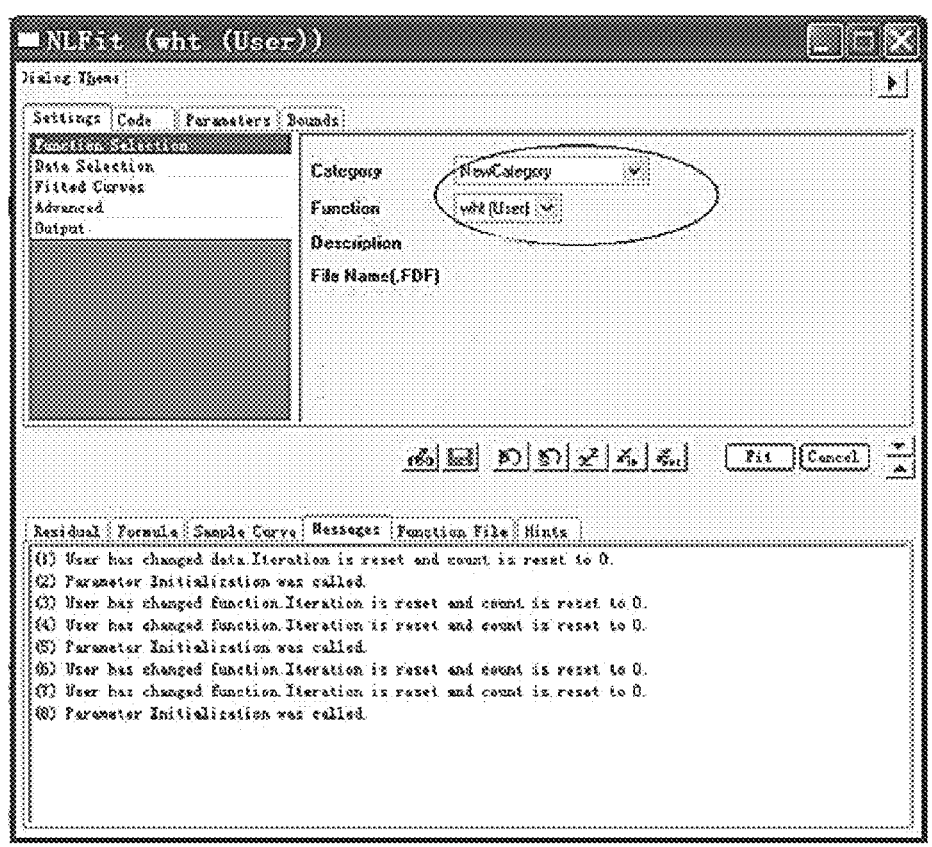
FIG. 14 is a screenshot for setting nonlinear fitting by software of a preferred embodiment in the present invention.
Figure 15:
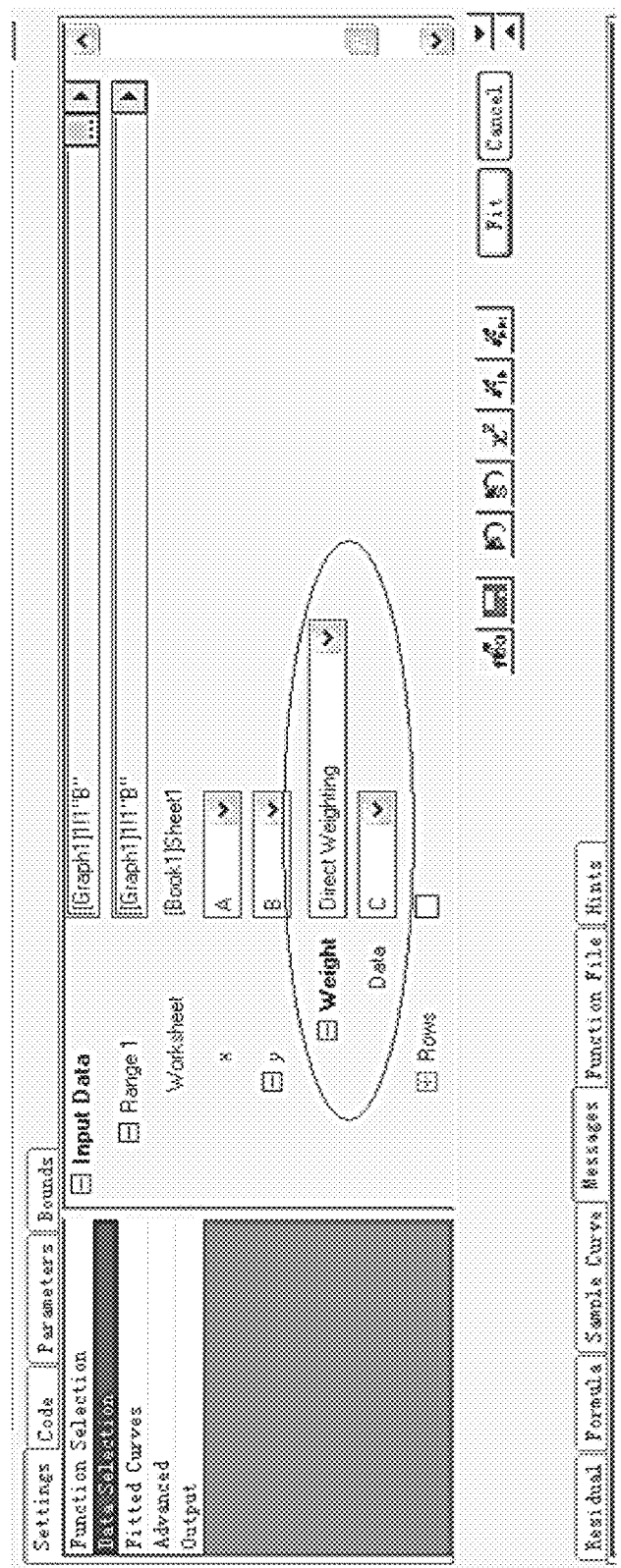
FIG. 15 is a screenshot for setting fitting weighting parameters by software of a preferred embodiment in the present invention.

Then names were set respectively in the dialog boxes of "Category" and "Function", such as the NewCategory and wht (User) in FIG. 14.

Step 3: fitting requirements were set in the "Data Selection" under the "Setting", and the "Direct Weighting" was selected in the dialog box of "Weight", and C in the "Data" was selected, which was shown as FIG. 14.

Figure 16:
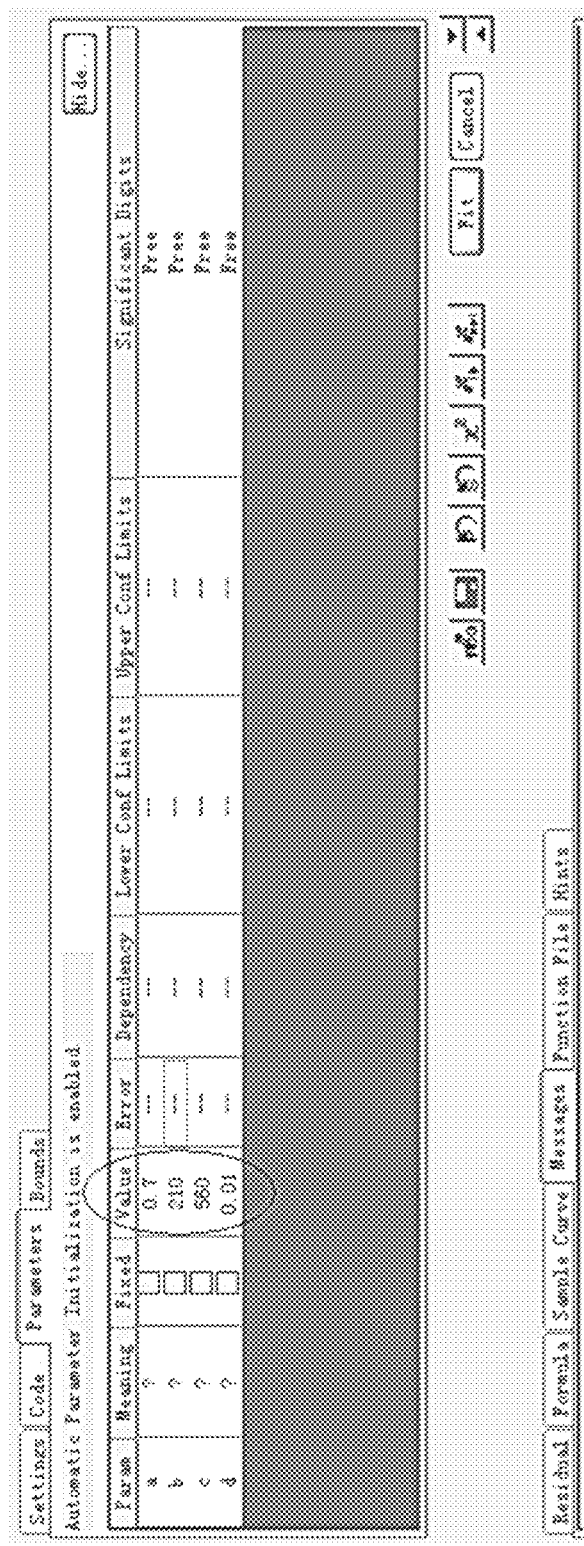
FIG. 16 is a screenshot for setting initial values to a custom function by software of a preferred embodiment in the present invention.
Figure 17:
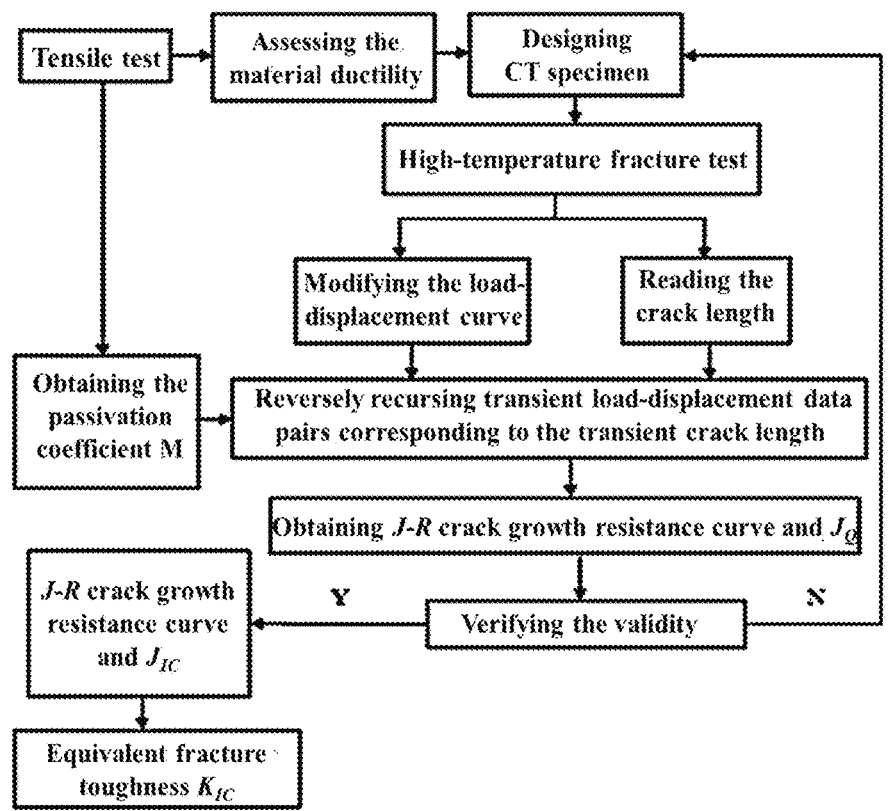
FIG. 17 is a flowchart of the method of a preferred embodiment in the present invention.
Figure 18:
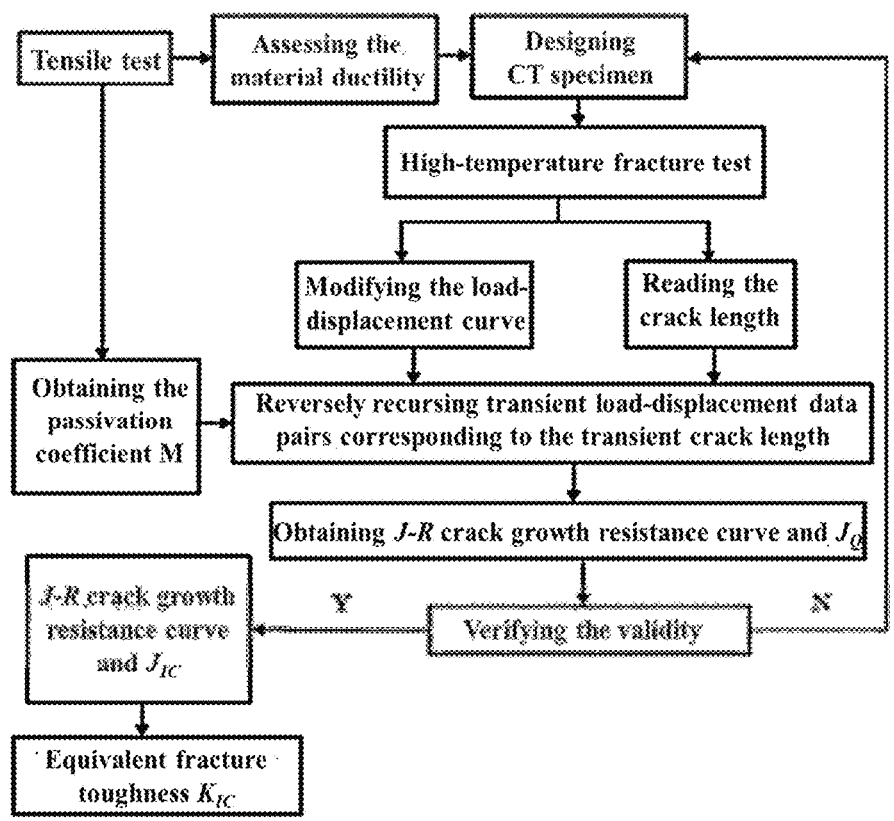

Step 4: initial values were set for the parameters of the custom function, then the fitting was carried on. The initial values were set in the "Value" under the "Parameters". In FIG. 16, the values were set as 0.7, 210, 560 and 0.01 respectively. After the setting was finished, click the "Fit" and the fitted function which met the requirements was obtained through multiple iterations.

It is to be understood for those skilled in the art that the foregoing description of the preferred embodiments is merely for illustration. The protection scope of the present invention is determined by the accompanying claims. Within the principles and spirits of the present invention, those skilled in the art may make various changes or modifications to these embodiments, but such changes and modifications all fall into the protection scope of the present invention.

What is claimed is:

1. A method of measurement and determination on fracture toughness of structural materials at high temperature, comprising the steps of:
   conducting a high-temperature tensile test on a standard tensile specimen of a structural material to obtain high-temperature tensile mechanical properties of the structural material, and determining that the structural material exhibits a ductile fracture behavior;
   preliminarily estimating the fracture toughness $K_{IC}$ of a compact tension (CT) specimen of the structural material at high temperature to obtain width (W) and thickness (B) of the CT specimen, wherein, $$J_{IC} = \frac{K_{IC}^2(1-v^2)}{E},$$

$$W = a_0 + b_0 \geq 2 \times 10 J_{IC}/\sigma_Y,$$

$$\sigma_Y = \frac{(\sigma_{ys} + \sigma_{uts})}{2},$$

$$2 \leq W/B \leq 4$$

E, v stand for elastic modulus and Poisson ratio of the structural material respectively, the unit of E is MPa; $a_0$, $b_0$ stand for initial average crack length and initial ligament size of the CT specimen respectively, the unit is mm, $\sigma_{ys}$, $\sigma_{uts}$ stand for yield strength and tensile strength of the structural material respectively, the unit is MPa;

inducing a fatigue crack with a length of 1.0~2.0 mm on the CT specimen through a high frequency fatigue testing machine, then grooving a side slot with a depth of 10% B at both sides of the CT specimen with a crack surface along the thickness direction;

measuring the thickness (B) and width (W) of the CT specimen, and placing the CT specimen into a heating equipment with a furnace having an upper, lower and middle part, and heating;

turning on an INSTRON or MTS testing machine, monotonic loading the CT specimen, and obtaining a load-displacement curve of the CT specimen by a load displacement transmission device on the testing machine;

cooling the CT specimen to room temperature, opening the furnace's cavity, tensing the CT specimen till fracture through a testing machine, then measuring an initial crack length $a_0^i$ and a final average crack length $a_f^i$ at nine spots on the crack surface by an optical microscopy or a camera to obtain an initial average crack length $a_0$ and a final crack length $a_f$ of the crack, wherein, $$a_0 = \frac{1}{8}\left[\frac{1}{2}(a_0^1 + a_0^9) + \sum_{i=2}^{8} a_0^i\right],$$

$$a_f = \frac{1}{8}\left[\frac{1}{2}(a_f^1 + a_f^9) + \sum_{i=2}^{8} a_f^i\right];$$

obtaining an initial elastic compliance $C_{LL(a_0)}$ of the CT specimen based on the sizes of the CT specimen and the crack and the elasticity modulus E of the structural material at high temperature, wherein, $$C_{LL(a_0)} = \frac{1}{EB_e}\left(\frac{W+a_0}{W-a_0}\right)^2\left[2.1360 + 12.219\left(\frac{a_0}{W}\right) - 20.065\left(\frac{a_0}{W}\right)^2 - 0.9925\left(\frac{a_0}{W}\right)^3 + 20.609\left(\frac{a_0}{W}\right)^4 - 9.9314\left(\frac{a_0}{W}\right)^5\right],$$

$B_e$ stands for an effective thickness of the CT specimen, the unit for which is mm;

modifying for testing errors comprising those caused by load contacts, local indentation, piston rigidity of the testing machine and rigidity of fixture, on the load-displacement curve to obtain a modified load-displacement curve;

calculating a passivation coefficient M of the structural material according to the tensile mechanical properties of the structural material;

calculating a modified crack length $a_{b(i)}$ corresponding to each load spot based on the modified load-displacement curve, the initial average crack length $a_0$ and the passivation coefficient M of the structural material, wherein, $$f\left(\frac{a_0}{W}\right) = \frac{\left[\left(2+\frac{a_0}{W}\right)\left(0.886+4.64\left(\frac{a_0}{W}\right)-13.32\left(\frac{a_0}{W}\right)^2+14.72\left(\frac{a_0}{W}\right)^3-5.6\left(\frac{a_0}{W}\right)^4\right)\right]}{\left(1-\frac{a_0}{W}\right)^{1.5}},$$

$$K_{(i)} = \frac{P_i}{(BB_N W)^{0.5}} f\left(\frac{a_0}{W}\right),$$

$$J_{el(i)} = \frac{K_{(i)}^2(1-v^2)}{E},$$

$$A_{pl(i)} = A_i - A_{el(i)} = A_i - \frac{P_i^2}{2k},$$

$$\eta_{pl} = 2 + 0.522 b_0/W = 2 + 0.522(W-a_0)/W,$$

$$J_{pl(i)} = \frac{\eta_{pl} A_{pl(i)}}{B_N b_0},$$

$$J_i = J_{el(i)} + J_{pl(i)},$$

$$a_{b(i)} = a_0 + \frac{J_i}{M\sigma_Y},$$

$A_i$ stands for a total area surrounded by each load spot on the load-displacement curve, $A_{el(i)}$, $A_{pl(i)}$ stand for an elastic area and a plastic area corresponding to each load spot respectively, k stands for elastic segment slope on the load-displacement curve;

calculating a nominal load $P_N$ and a nominal displacement $V_{pl}$, wherein, $$P_{N(i)} = \frac{P_i}{WB[1-a_{b(i)}/W]^{\eta_{pl}}},$$

$$P_{N(f)} = \frac{P_f}{WB[1-a_f/W]^{\eta_{pl}}},$$

$$C_{LL(a_i)} = \frac{1}{EB_e}\left(\frac{W+a_{b(i)}}{W-a_{b(i)}}\right)^2 \left[2.1630 + 12.219\left(\frac{a_{b(i)}}{W}\right) - 20.065\left(\frac{a_{b(i)}}{W}\right)^2 - 0.9925\left(\frac{a_{b(i)}}{W}\right)^3 + 20.609\left(\frac{a_{b(i)}}{W}\right)^4 - 9.9314\left(\frac{a_{b(i)}}{W}\right)^5\right],$$

$$V_{pl(i)} = \frac{V_i - P_i C_{LL(a_i)}}{W},$$

$$C_{LL(a_f)} = \frac{1}{EB_e}\left(\frac{W+a_f}{W-a_f}\right)^2 \left[2.1630 + 12.219\left(\frac{a_f}{W}\right) - 20.065\left(\frac{a_f}{W}\right)^2 - 0.9925\left(\frac{a_f}{W}\right)^3 + 20.609\left(\frac{a_f}{W}\right)^4 - 9.9314\left(\frac{a_f}{W}\right)^5\right],$$

$$V_{pl(f)} = \frac{V_f - P_f C_{LL(a_f)}}{W},$$

forming data pairs $(V_{pl(i)}, P_{N(i)})$ $(V_{pl(f)}, P_{N(f)})$, wherein $V_{pl(f)}$ and $P_{N(f)}$ stand for nominal displacement and load corresponding to a final spot respectively, which are calculated by the final average crack length $a_f$;

obtaining a four-parameter fitted equation based on the effective nominal load-displacement data pairs, specifically comprising removing the data pairs of the nominal plastic displacement and the nominal load corresponding to spots which satisfy $V_{pl(i)} < 0.001$, removing the data pairs of the nominal plastic displacement and the nominal load corresponding to the spots located in the range after the maximum nominal load and before the final spot, plotting the remaining data pairs of the nominal plastic displacement and the nominal load and the data pair $(V_{pl(f)}, P_{N(f)})$ corresponding to the final spot in origin software, and customizing a four-parameter equation, fitting the valid data on a curve according to the four-parameter equation, wherein the four-parameter equation is as below:

$$P_{N(i)} = \frac{a + bV_{pl(i)} + cV_{pl(i)}^2}{d + V_{pl(i)}};$$

reversely recursing load-displacement data pairs $(V_i, P_i)$ corresponding to an actual crack length $a_i$ based on the four-parameter equation;

calculating a J_R crack extension resistance curve of the CT specimen based on the actual crack length $a_i$ and the load-displacement data pairs $(V_i, P_i)$ according to ASTM E1820, specifically comprising obtaining an elastic compliance $C_{LL(a_i)}$ corresponding to the actual crack length $a_i$, driving force $J_{pl(i)}$, $J_{el(i)}$, $J_i$ crack tip, and crack extension length $\Delta a_i$, wherein, $$V_{pl(i)} = V_i - P_i C_{LL(a_i)},$$

$$A_{pl(i)} - A_{pl(i-1)} = \frac{[P_{(i)} + P_{(i-1)}][V_{pl(i)} - V_{pl(i-1)}]}{2},$$

$$\eta_{(i-1)} = 2.0 + 0.522 b_{(i-1)}/W,$$

$$\gamma_{(i-1)} = 1.0 + 0.76 b_{(i-1)}/W,$$

$$J_{pl(i)} = \left[J_{pl(i-1)} + \left(\frac{\eta_{(i-1)}}{b_{(i-1)}}\right)\frac{A_{pl(i)} - A_{pl(i-1)}}{B_N}\right]\left[1 - \gamma_{(i-1)}\frac{a_{(i)} - a_{(i-1)}}{b_{(i-1)}}\right],$$

$$\Delta a_i = a_i - a_0,$$

plotting the crack extension length $\Delta a_i$ and the driving force on the crack tip $J_i$ in the figure, and fitting a curve according to the power-law function $y=ax^b$ to obtain a J_R crack extension resistance curve of the structural material;

examining the validity of the J_R crack extension resistance curve, wherein, when the data obtained meet the following requirements, the J_R crack extension resistance curve is valid:

the difference between the initial crack length $a_0^i$ and the initial average crack length $a_0$ of each spot tested by the nine-spot method is less than 0.05 B, the difference between the final crack length $a_f^i$ and the final average crack length $a_f$ of each spot tested by the nine-spot method is less than 0.05 B, the $J_i$ on the crack tip of the CT specimen is less than $J_{max}$, wherein $J_{max}=\min\{b_0\sigma_Y/10, B\sigma_Y/10\}$, the crack extension length $\Delta a_i$ of the CT specimen is less than $\Delta a_{max}$, wherein $\Delta_{max}=0.25\, b_0$;

when the data obtained do not meet the requirements above, the J_R crack extension resistance curve is invalid, then re-estimating the fracture toughness $J_{IC}$ of the structural material and redesigning the CT specimen, and repeating the tests and analysis according to this step and the previous steps until the data obtained meet the requirements above;

calculating passivation line, limit line and valid data area, and determining the $J_Q$ in the J_R crack extension resistance curve;

if the thickness, the initial ligament length and the slope of the initial cracking spot of the CT specimen satisfy the formula $B>10J_Q/\sigma_Y$, $b_0>10J_Q/\sigma_Y$ and $\Delta a=\Delta a_Q$, $dJ/da(\Delta a_Q)<\sigma_Y$ respectively and thus $J_Q=J_{IC}$; otherwise, the $J_Q$ tested is related to the geometrical size, then re-estimating the fracture toughness $J_{IC}$ of the CT specimen and redesigning the CT specimen, and repeating tests and analysis according to this step and the previous steps until the $J_Q$ obtained meets the requirements, then the fracture toughness $J_{IC}$ of the structural material is obtained;

calculating the fracture toughness per equivalent of the structural material $K_{IC}$, and obtaining the fracture toughness per equivalent of the structural material $K_{IC}$ according to the formula $K_{IC}=\sqrt{J_{IC}E/(1-v^2)}$.

2. The method of measurement and determination on fracture toughness of structural materials at high temperature according to claim 1, wherein the step of conducting a high temperature tensile test further comprises preliminarily assessing the fracture behavior of the structural material through a stress-strain curve and fracture morphology, and determining whether the structural material exhibits a ductile fracture behavior according to a value which is obtained by dividing the strain corresponding to the tensile strength on the stress-strain curve with fracture strain and whether a fracture surface of the tensile specimen exhibits obvious dimple features.

3. The method of measurement and determination on fracture toughness of structural materials at high temperature according to claim 1, wherein the heating equipment is installed in an INSTRON or a MTS testing machine.

4. The method of measurement and determination on fracture toughness of structural materials at high temperature according to claim 1, wherein the step of measuring the thickness (B) and the width (W) further comprise placing three thermocouples in the upper, middle and lower part of the furnace wherein the thermocouple in the middle part is close to the crack tip region of the CT specimen, and keeping heated, when the upper, middle and lower thermocouples reach an average value of a set temperature, maintaining this temperature for half an hour before the heating has finished.

* * * * *